United States Patent
Djakov et al.

(10) Patent No.: US 9,551,702 B2
(45) Date of Patent: Jan. 24, 2017

(54) MICROCANTILEVER SENSOR WITH BIMORPH ACTUATION AND PIEZORESISTIVE READ-OUT

(75) Inventors: Vladislav Djakov, Denbighshire (GB); Richard Dunn, Denbighshire (GB)

(73) Assignee: MICROVISK LIMITED, St Asaph (GB)

( * ) Notice: Subject to any disclaimer, the term of this patent is extended or adjusted under 35 U.S.C. 154(b) by 323 days.

(21) Appl. No.: 14/119,874

(22) PCT Filed: May 25, 2012

(86) PCT No.: PCT/GB2012/051196
§ 371 (c)(1),
(2), (4) Date: Nov. 24, 2013

(87) PCT Pub. No.: WO2012/160393
PCT Pub. Date: Nov. 29, 2012

(65) Prior Publication Data
US 2015/0160200 A1    Jun. 11, 2015

(30) Foreign Application Priority Data
May 25, 2011 (GB) .................................. 1108814.3

(51) Int. Cl.
*G01N 33/53* (2006.01)
*G01N 33/543* (2006.01)
(Continued)

(52) U.S. Cl.
CPC ........ *G01N 33/5304* (2013.01); *G01N 27/128* (2013.01); *G01N 29/022* (2013.01); *G01N 33/5438* (2013.01); *G01N 33/54373* (2013.01)

(58) Field of Classification Search
CPC ............ G01N 33/5304; G01N 33/5438; G01N 33/54373; G01N 29/022; G01N 27/128
See application file for complete search history.

(56) References Cited

U.S. PATENT DOCUMENTS 6,096,559 A    8/2000 Thundat et al.
2002/0139190 A1    10/2002 Daraktchiev et al.
(Continued)

FOREIGN PATENT DOCUMENTS

EP    1617211 A1    1/2006
GB    2437753 A    11/2007
(Continued)

OTHER PUBLICATIONS

International Preliminary Report on Patentability for International Patent Application No. PCT/GB2012/051196, mailed on Dec. 5, 2013, 7 pages.
(Continued)

*Primary Examiner* — Melanie Y Brown
(74) *Attorney, Agent, or Firm* — Shichrur & Co.

(57) ABSTRACT

There is provided a method of monitoring one or more specified reactions in a fluid medium sample using a thermal signature, comprising providing at least one micro-cantilever sensor, said micro-cantilever sensor comprising at least two materials having different coefficients of thermal expansion, and having a heater and piezo-resistive sensor integrated therein, calibrating the at least one micro-cantilever response to thermal changes to form a calibrated micro-cantilever response characteristic, starting the specified reaction in the fluid medium sample, pulsing the heater with one or more electrical pulses to induce heat generation in the micro-cantilever, sampling the output of the integrated piezo-resistive sensor to characterize a response of the micro-cantilever during the specified reaction in the fluid medium, and subtracting the calibrated micro-cantilever response characteristic from the sampled output to determine a characteristic of the one or more specified reactions in the fluid medium sample. There is also provided a method for measuring at least one thermal property of a fluid
(Continued)

medium sample, and a fluid medium sample reaction detection apparatus.

11 Claims, 10 Drawing Sheets

(51) Int. Cl.
*G01N 29/02* (2006.01)
*G01N 27/12* (2006.01)

(56) References Cited

U.S. PATENT DOCUMENTS

| | | | |
|---|---|---|---|
| 2006/0257286 A1* | 11/2006 | Adams | G01N 29/022 422/82.01 |
| 2007/0138909 A1 | 6/2007 | Mortet et al. | |
| 2008/0068000 A1 | 3/2008 | Bargatin et al. | |
| 2008/0085212 A1* | 4/2008 | Adams | G01N 29/036 422/50 |
| 2009/0139340 A1 | 6/2009 | King et al. | |
| 2010/0251806 A1 | 10/2010 | Djakov et al. | |
| 2014/0147337 A1* | 5/2014 | Urey | G01N 29/022 422/69 |

FOREIGN PATENT DOCUMENTS

| | | |
|---|---|---|
| WO | 2004029625 A2 | 4/2004 |
| WO | 2007011364 A1 | 1/2007 |
| WO | 2010021380 A1 | 2/2010 |

OTHER PUBLICATIONS

International Search Report and Written Opinion for PCT/GB2012/051196, mailed on Aug. 31, 2012, 11 pages.
Search Report for Great Britain Patent Application No. GB1108814.3, mailed on Sep. 12, 2011, 3 pages.
Further Search Report for Great Britain Patent Application No. GB1108814.3, mailed on Oct. 12, 2011, 1 page.
Examination Report for Great Britain Patent Application No. GB1108814.3, mailed on Oct. 13, 2011, 4 pages.
Examination Report for Great Britain Patent Application No. GB1108814.3, mailed on Jun. 6, 2012, 1 page.

* cited by examiner

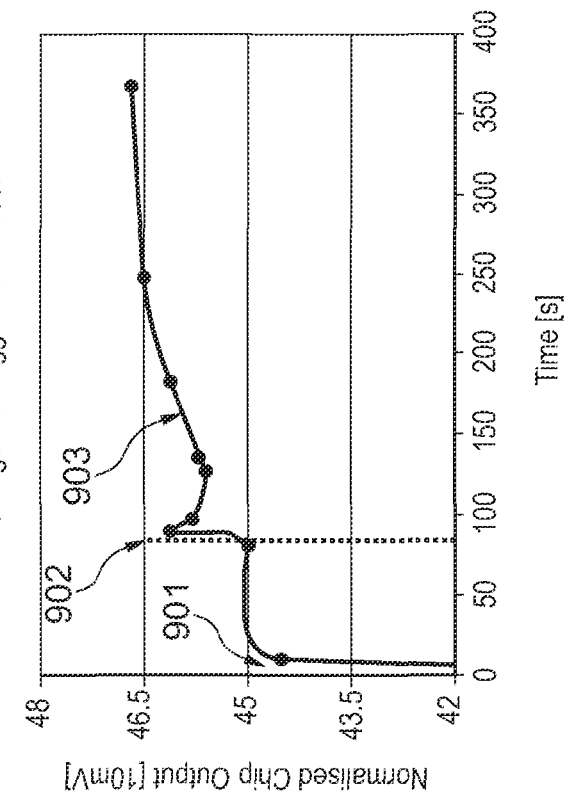
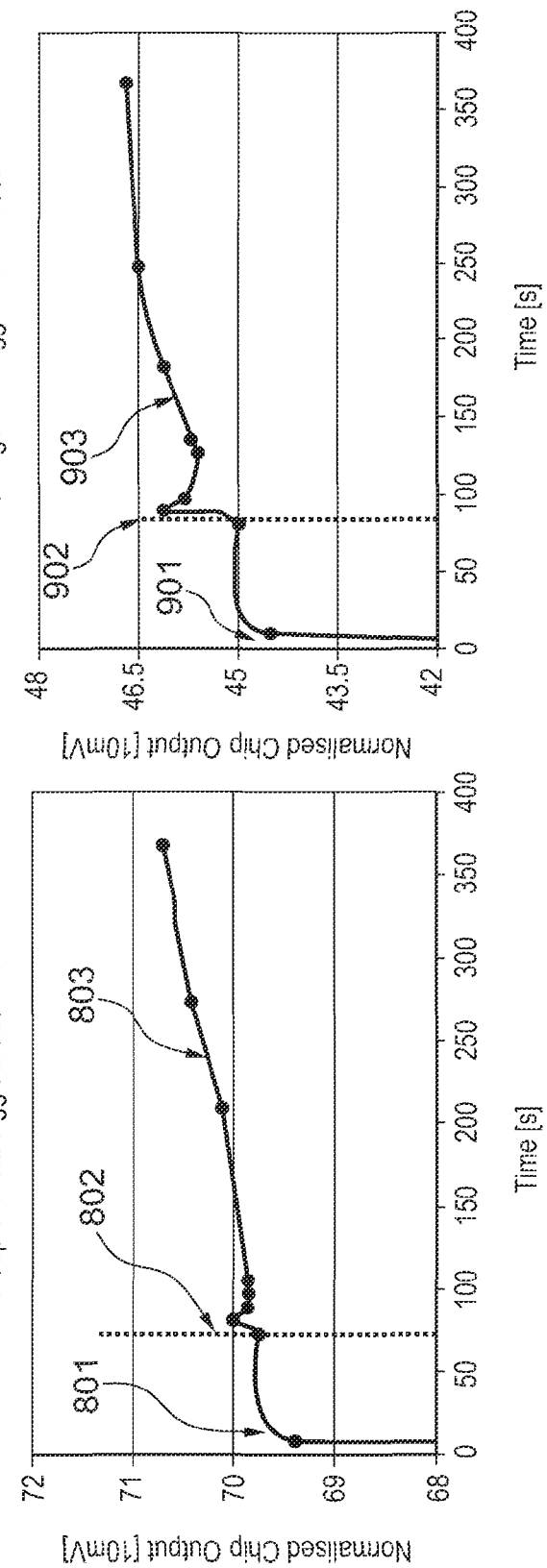
Fig. 8
Fig. 9

MICROCANTILEVER SENSOR WITH BIMORPH ACTUATION AND PIEZORESISTIVE READ-OUT

CROSS REFERENCE

This application is a National Phase Application of PCT International Application No. PCT/GB2012/051196, International Filing Date May 25, 2012, which in turn claims priority from GB Patent application No. 1108814.3, filed May 25, 2011, the entire disclosures of which are incorporated herein by reference.

FIELD OF THE INVENTION

This invention relates to methods and measurement devices for measuring a property of a fluid medium in general, and in particular to determining interactions of or within a fluid medium, such as antigen antibody interactions, using a self-sensing micro-actuator fluid probe in particular.

BACKGROUND OF THE INVENTION

There are many useful chemical and biological reactions that take place within a fluid medium. These may be the result of interaction between the fluid medium and the surrounding environment, e.g. oxidation when exposed to air, or they may be a result of mixing the fluid medium with some reagent or another fluid medium containing a reagent. Such chemical and biological reactions may be useful in a variety of areas, such as industrial processing, medical diagnostics, or the like. The use of such chemical and biological reactions often requires suitable measurement equipment, to ascertain whether a particular specified reaction has actually taken place, or further, to provide a measure of the extent of occurrence of the reactions.

There are known methods to measure the existence or extent of reactions within a fluid medium, but they each have associated disadvantages, including speed or accuracy limitations, cost or complexity to carry out, and the like. For example, whilst the binding of specific antibodies and antigens in a fluid medium can be detected using additional tagging techniques, these techniques may change the structure and affinity of binding. Meanwhile, labelling also requires complexity and amplification of weak signals. Label-free methods, where tagging is not used, can be based on methods such as surface plasmon resonance, but these methods lack the ability to carry out multiple parallel tests to allow for measuring several reactions in a hand held device.

SUMMARY OF THE INVENTION

The present invention provides a method of monitoring one or more specified reactions in a fluid medium sample using a thermal signature, said method comprising providing at least one micro-cantilever sensor, said micro-cantilever sensor comprising at least two materials having different coefficients of thermal expansion, and having a heater and piezo-resistive sensor integrated therein, calibrating the at least one micro-cantilever response to thermal changes to form a calibrated micro-cantilever response characteristic, starting the specified reaction in the fluid medium sample, pulsing the heater with one or more electrical pulses to induce heat generation in the micro-cantilever, sampling the output of the integrated piezo-resistive sensor to characterise a response of the micro-cantilever during the specified reaction in the fluid medium, and subtracting the calibrated micro-cantilever response characteristic from the sampled output to determine a characteristic of the one or more specified reactions in the fluid medium sample.

The method may also be used to monitor non-specified reactions, or properties (or changes in properties) of the fluid medium sample, such as thermal properties, over time.

Optionally, the one or more specified reactions include any one or more of: a covalent reaction; a non-covalent reaction; a binding reaction; a non-binding reaction; an antibody-antigen reaction; an agglutination reaction; a blood typing reaction.

Optionally, the characteristic of the one or more specified reactions in the fluid medium response is the presence or not, or extent, of the one or more specified reactions.

Optionally, the method may further comprise coating at least one micro-cantilever with a reagent for at least one of the one or more specified reactions.

Optionally, the method may further comprise providing at least two substantially similar micro-cantilevers, wherein one is coated with a reagent, and one is uncoated, wherein the method further comprises comparing the output of a piezo-resistive sensor integrated into the coated micro-cantilever with the output of a piezo-resistive sensor integrated into the uncoated micro-cantilever when both are immersed in the fluid medium sample.

There is also provided a method for measuring at least one thermal property of a fluid medium sample, comprising providing at least one micro-cantilever sensor, said micro-cantilever sensor comprising at least two materials having different coefficients of thermal expansion, and having a heater and piezo-resistive sensor integrated therein, calibrating the at least one micro-cantilever response to thermal changes of a known fluid medium sample to form a calibrated micro-cantilever response characteristic, immersing at least a free end portion of the at least one micro-cantilever sensor into the unknown fluid medium sample, pulsing the heater with one or more electrical pulses to induce heat generation in the micro-cantilever, sampling the output of the integrated piezo-resistive sensor to characterise a response of the micro-cantilever in the fluid medium, and subtracting the calibrated micro-cantilever response characteristic from the sampled output to determine the thermal conductivity of the fluid medium sample.

Optionally, the at least one thermal property of the fluid is any one or more of: thermal conductivity; heat capacity; temperature; volumetric heat capacity; and thermal diffusivity.

Optionally, the calibrating of the at least one micro-cantilever response may comprise immersing the at least one micro-cantilever in a plurality of test fluid medium samples having known rheological and thermal properties, pulsing the at least one micro-cantilever with at least one electrical pulse to induce heat generation in the micro-cantilever and sampling the output of the integrated piezo-resistive sensor to characterise a response of the micro-cantilever in each of the test fluid medium samples.

Optionally, the calibrating of the at least one micro-cantilever response may comprise providing an extended length pulse to the at least one micro-cantilever to provide a steady state thermal transfer characteristic response for the at least one micro-cantilever, or fluid medium sample.

Optionally, operation of the at least one micro-cantilevers during testing may be operable to accelerate a reaction occurring within the fluid medium sample under test.

There is also provided apparatus adapted to carry out any of the described methods, wherein the apparatus response is pre-characterised such that the apparatus may be used to characterise a fluid medium sample, or reactions therein or therewith.

There is still further provided a fluid medium sample reaction detection apparatus, comprising a first uncoated micro-cantilever sensor, a second, coated, micro-cantilever sensor, and circuitry operable (and calibrated) to detect a difference in response to one or more electrical input pulses to the first and second micro-cantilevers when said micro-cantilevers are immersed in a fluid medium sample under test, wherein the coated and uncoated micro-cantilevers are substantially identically formed from at least two materials having different coefficients of thermal expansion, and having an integrated heater and piezo-resistive sensor therein, said micro-cantilevers exhibiting substantially similar characteristic responses to an input electrical pulse prior to coating, and wherein a coating on the second coated micro-cantilever causes or accelerates the reaction to be detected.

Optionally, a free movable end of the first and second micro-cantilevers are positioned opposite and adjacent or above/below one another, within a shared container for the fluid medium sample under test.

Optionally, the coating is antigen or antibody, and the reaction is a specified antibody-antigen reaction.

Optionally, the antibody-antigen reaction is an agglutination of blood reaction.

Optionally, the extended length pulse may be a pulse with, e.g. >50 ms pulse width, and with low average power, where the specific value of low average power used may be dependent on the specific form of actuator used within the bi-morph micro-cantilever. This is because the exact amount of energy required to move the micro-cantilever a certain distance is dependent overall construction of the micro-cantilever. However, functionally, low average power should ensure there is no over deformation, or irreversible deformation of the bi-morph micro-cantilever.

Embodiments of the invention provide methods comprising providing at least one calibrated micro-cantilever sensor, said micro-cantilever sensor comprising at least two materials having different coefficients of thermal expansion, and having a heater and piezo-resistive sensor integrated therein, said at least one calibrated micro-cantilever sensor being calibrated to thermal and/or mechanical changes, and a free end of said at least one micro-cantilever being operable to immerse into the fluid medium sample, pulsing the heater with one or more electrical pulses to induce heat generation in the micro-cantilever, and sampling the output of the integrated piezo-resistive sensor to provide a response of the micro-cantilever during the specified reaction in the fluid medium to characterise one or more properties of the fluid medium sample and/or reaction therein.

Embodiments of the invention also relate to methods and measurement devices for measuring multiple/several properties of a fluid medium simultaneously from a single measurement, or single pulse, or series suitably shaped pulses (e.g. relatively long or short pulses, or a combination of the two, thereby allowing for both steady state (thermal) and mechanical aspects to be measured and/or characterised.

Embodiments of the present invention also provide a method of monitoring one or more specified reactions in a fluid medium sample using simultaneous measurement of multiple physical properties from combination of thermal and mechanical response characteristics, said method comprising providing at least one micro-cantilever sensor, said micro-cantilever sensor comprising at least two materials having different coefficients of thermal expansion, and having a heater and piezo-resistive sensor integrated therein, calibrating the at least one micro-cantilever response to thermal and mechanical changes to form a calibrated micro-cantilever response characteristic, starting the specified reaction in the fluid medium sample, pulsing the heater with one or more electrical pulses to induce heat generation in the micro-cantilever wherein the operation is tuned to the physical nature of the reaction (e.g. in the fluid volume, or in proximity to the probe, or on the surface of the probe), sampling the output of the integrated piezo-resistive sensor to characterise a response of the micro-cantilever during the specified reaction in the fluid medium, and subtracting the calibrated micro-cantilever response characteristic from the sampled output to determine a characteristic of the one or more specified reactions in the fluid medium sample.

Embodiments also provided a method for measuring simultaneous thermal and/or rheological physical properties of a fluid medium sample. These embodiments may comprise providing at least one micro-cantilever sensor, said micro-cantilever sensor comprising at least two materials having different coefficients of thermal expansion, and having a heater and piezo-resistive sensor integrated therein, calibrating the at least one micro-cantilever response to thermal and mechanical changes in known fluid medium samples to form calibrated micro-cantilever response characteristics (for example, the transient profile of the response signal and the absolute change in signal), immersing at least a free end portion of the at least one micro-cantilever sensor into the unknown fluid medium sample, pulsing the heater with one or more electrical pulses to induce heat generation in the micro-cantilever, sampling the output of the integrated piezo-resistive sensor to characterise a response of the micro-cantilever in the fluid medium, and calculating the calibrated micro-cantilever response characteristic from the sampled output to determine simultaneously the thermal and mechanical properties of the fluid medium sample.

Optionally, the at least one thermal and mechanical property of the fluid is any one or more of: thermal conductivity; heat capacity; temperature; volumetric heat capacity; thermal diffusivity; viscosity; density; shear rate; and flow rate.

Embodiments also provide testing apparatus comprising at least one micro-cantilever. These may be arranged to carry out any herein described method. The late least one micro-cantilever may be (pre-use) calibrated at manufacture, with a digital memory operably coupled to the micro-cantilever, and/or a reading device and/or a removal cartridge containing the at least one micro-cantilever, for use with the reading device, such that the (pre-use) calibration is available for subtraction/comparison with outputs of the micro-cantilever during use in any described methods.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 8 shows an output signal from a micro-cantilever sensor according to an embodiment of the invention for a first specified agglutination test;

FIG. 9 shows an output signal from a micro-cantilever sensor according to an embodiment of the invention for a second specified agglutination test;

DETAILED DESCRIPTION OF THE PREFERRED EMBODIMENTS

Embodiments of the present invention provide an excitation and measurement device for one or more specified interactions within a fluid medium sample (such as specific antigen-antibody interactions, or the like), using a self-sensing thermal micro-actuator or multi-parameter fluid probe, as described in more detail below. The described micro-actuator based sensor probe is disclosed in the form of a micro-cantilever, or beam, but other physical forms of sensor may be realised.

The term 'fluid medium sample' used herein may refer to either a singular fluid or a combination of two or more fluids, or a mixture of one or more fluids with another medium causing a reaction. The term 'fluid medium sample' may also include physical or complex suspensions in the one or more fluid(s), for example particulate suspensions comprising both solid portions as well as the fluid(s), such as liquids or gas. The particulates may be the interactive portion of the fluid medium sample, for example when they are formed as a coagulate or the like. In a broad sense, the fluid medium sample may be any chemical sample, or biologic sample taken from a specimen, suitable for testing.

The excitation and measurement device may form part of a dynamic micro test/diagnostic system that is sensitive to the measurement of fluid medium properties, such as thermal, coagulation, or other properties and may provide a unique parallel function as a mixer (i.e. aiding the interactions in the fluid medium sample under test, and may also help to force convection of heat through the sample). The mixer function may allow for fast time to answer in biological and chemical reactions. Such a system is particularly applicable to measurements involving biological and chemical suspensions in a fluid. The disclosed method and device also has lower power requirements compared to standard known fluid medium sample thermal testing methods, such as the 'hot wire' test.

The design and fabrication of the micro-actuator of the micro test/diagnostic system may be such that it either solely works in thermal sensing mode, only in mechanical sensing mode, or as a hybrid sensor that performs both mechanical and thermal measurements. A plurality of such micro-actuator based sensors may be utilised together to form a differential sensor system as described in more detail below. The present description includes the results of experiments carried out on embodiments of the invention to assess the ability of the micro-actuator based method and measurement device(s) according to the invention to measure thermal or other properties of a fluid medium sample, its sensitivity compared to standard known measurement methods or devices, and particularly how to use such a micro-actuator as a sensor and mixer for fast antigen antibody interaction measurements.

Figure 1:
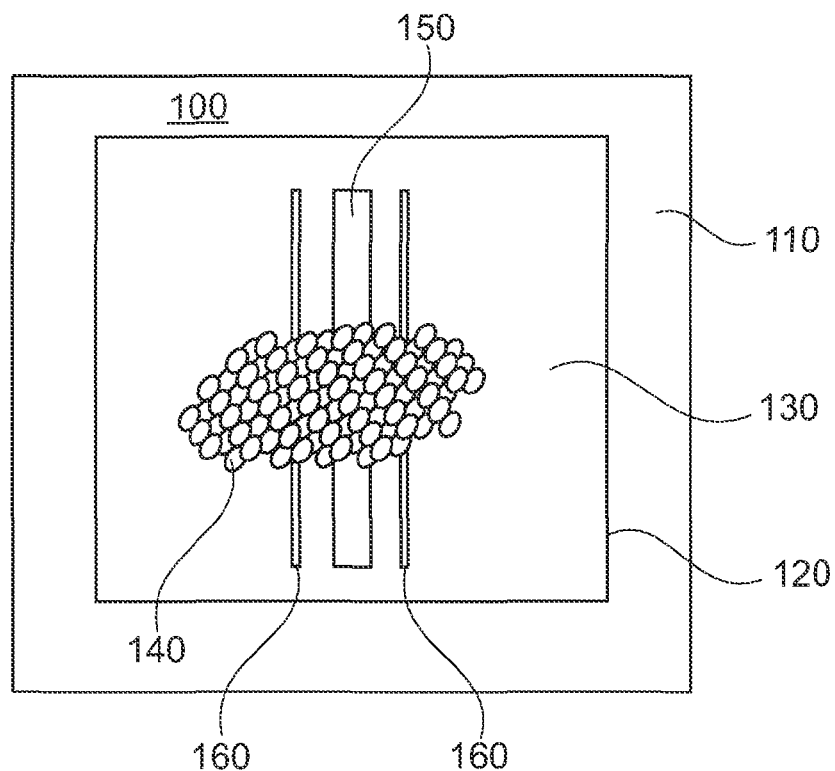
FIG. 1 shows a top down view of a prior art "hot wire" sensing system for determining a thermal property of fluid medium.

FIG. 1 shows a top down view of a prior art micro scale "hot wire" sensing system 100 for only determining a thermal property of fluid medium 130. It comprises a container 110, for containing the fluid medium sample 130, which may comprise a bulk fluid medium, potentially having a coagulating portion 140. The coagulating portion 140 may appear, and increase in size, weight or volume over time, as a reaction in the fluid medium sample starts and then proceeds.

The sensing portion of the sensing system 100 comprises the surface of the container 120 having a heater 150 formed thereon or in, with temperature sensors 160 also formed on or in the surface of the container 120, the temperature sensors being located adjacent but spaced apart from the heater 150. The sensors are arranged to detect a temperature, which is dependent on a combination of factors including the thermal characteristics of the fluid medium 130 sample under test, the container surface 120 thermal properties and the distance of the temperature sensors 160 from the heater 150, amongst other things.

Problems with this existing sensor system 100 include the fact that the because the sensors 160 are embedded on one side, within the surface of the container 120, the sensor 160 results may be materially affected by the temperature characteristics of the container material, and the like, and therefore mask or substantially deteriorate the results derived from the sensor 160. For example, where the heater and temperature sensors are on a substrate surface, there will be high conduction (heat loss) to the surface substrate. Furthermore, coagulates or suspensions may settle onto the sensor surface in short times (i.e. <30 seconds) where the fluid is static and held in a low volume (i.e. <1 micro-liter) chamber, materially altering (e.g. skewing) the efficiency or accuracy of detection process (as particularly shown in FIG. 2).

Figure 2:
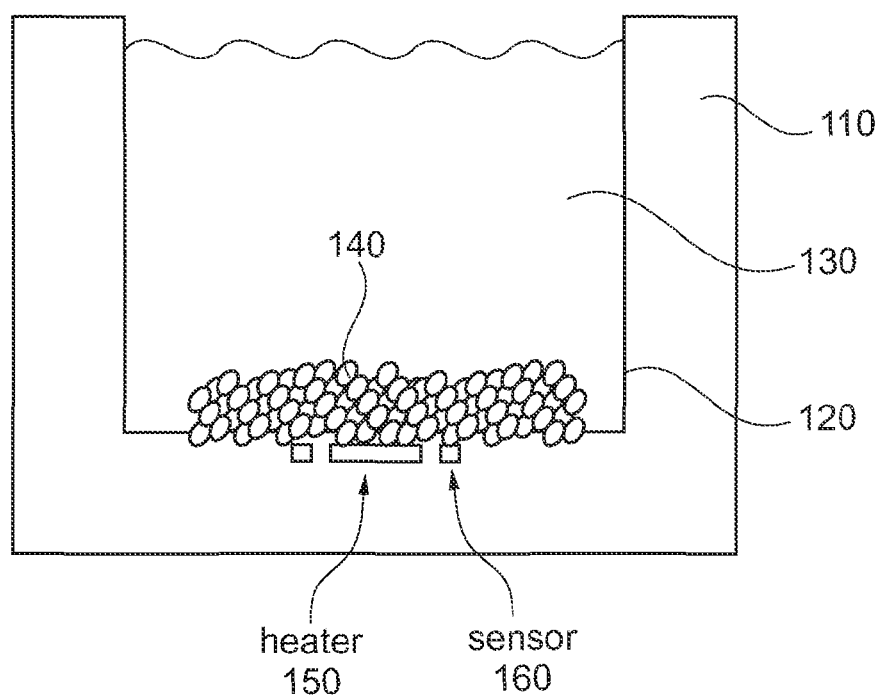
FIG. 2 shows a side view of the prior art "hot wire" sensing system of FIG. 1.

Moreover, only the region immediately adjacent the container surface 120 and fluid medium contact boundary 145 may be sensed. This may not be a true representation of the overall fluid medium sample being tested. FIG. 2 shows a side view of the same sensing system 100 as shown in FIG. 1, which more clearly shows the boundary condition sensing limitation, and how suspensions or coagulates may skew the results obtained. Moreover, it can be seen that there is no inherent mixing of the fluid medium function available.

Accordingly, the invention provides a dynamic micro-actuator with integrated sensor for detection of properties of a fluid medium sample, including specific antigen antibody interactions. Preferably, the micro-actuator is a micro-cantilever based sensor.

The micro-cantilever based sensor may be formed as a beam attached to a body by a first end, with a second end distance from the first that is free to move in relation to the body. The micro-cantilever beam typically has a rectangular surface area, with the longer side of the rectangle extending from the body. The micro-cantilever may comprise a laminate of at least two layers of material, the materials of each layer having different coefficients of thermal expansion (i.e. bi-morph). The materials can be different materials, or the same material processed (e.g. stressed) so as to have different coefficients of thermal expansion. One exemplary material suitable for forming the laminate of at least two layers is polyimide.

Under application of heat, one layer will expand more than the other for the same rise in temperature, and hence the micro-cantilever will bend in the direction of the material with the lower coefficient of thermal expansion. Upon cooling, one layer will contract faster than another for the same decrease in temperature, and hence the micro-cantilever will then bend in the direction of the material with the greater coefficient of thermal expansion.

An actuating heater may be located on or in the micro-cantilever, and may comprise conductive material forming a continuous line or track across an area of the surface of the micro-cantilever. The heater may further comprise electrical contacts for delivery of current to (and resulting in heat dissipation from) the heater. These electrical contacts may be located on an upper surface of the body, in use, for ease of access.

One or more integrated sensor(s) may also be located on or in the micro-cantilever, and may also comprise conductive material forming a continuous line or track across an area of the surface of the micro-cantilever.

Wheatstone bridge circuits may be used to measure the output of the integrated sensor(s), as they are a particularly sensitive apparatus for the comparative measurement of capacitance and resistance. A Wheatstone bridge circuit may be used with the micro-cantilever to determine the amount of movement (i.e. bending) of the micro-cantilever, or other properties (or change in properties) of the overall micro-cantilever sensor system, such as thermal properties. The Wheatstone bridge may be located on the body of the micro-cantilever, or remote from the micro-cantilever sensor, but coupled to electrical contacts of the respective parts of the micro-cantilever sensor, such as integrated sensors(s). In use, a voltage is applied across the Wheatstone bridge circuit, and a voltage output is measured across the middle. When the output of the bridge is zero, the bridge is said to be balanced and the resistances/capacitances equal. When the resistance/capacitance of one of the legs changes, due to a change in the output of the integrated sensor(s), the previously balanced bridge is now unbalanced. This unbalance causes a voltage to appear across the middle of the bridge, from which an output of the overall apparatus can be derived, indicative of a property (or change in property, or more than one property) of the fluid medium sample. When using resistive sensors, the resistance may change due to mechanical changes, thermal changes or both changes acting at the same time.

Figure 3:
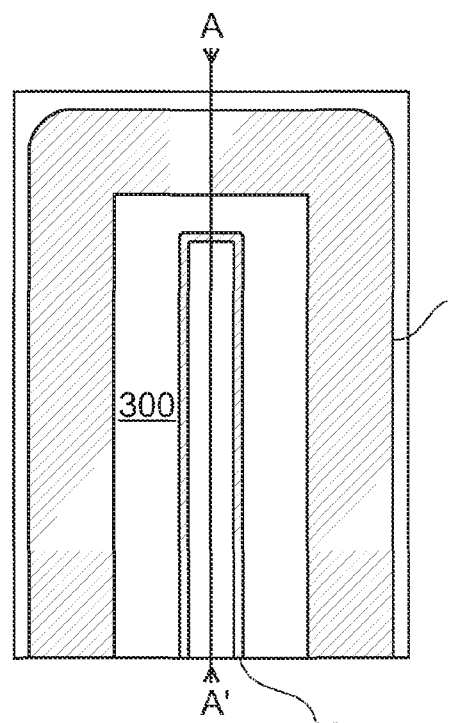
FIG. 3 shows a top down view of a micro-actuator based sensor according to an embodiment of the present invention.
Figure 4:
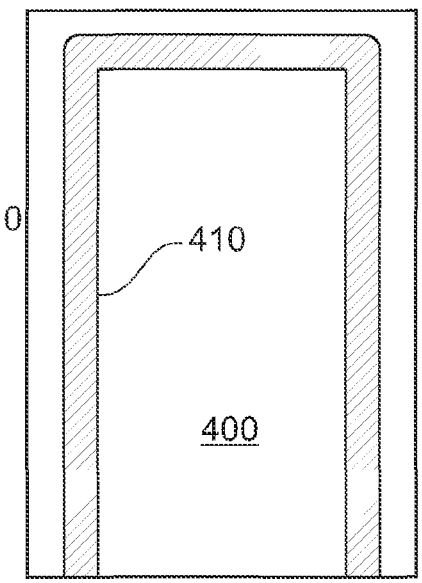
FIG. 4 shows a top down view of micro-actuator based sensor according to another embodiment of the present invention.
Figure 5:
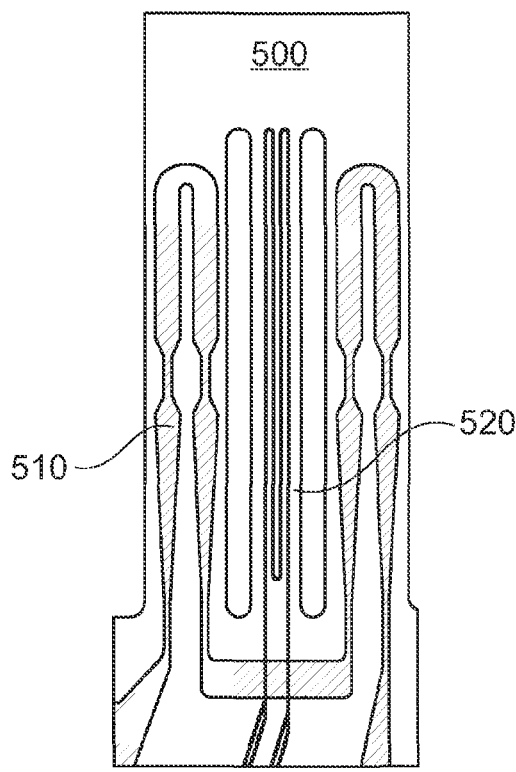
FIG. 5 shows a two top down views of micro-actuator based sensors according to other embodiments of the present invention, particularly showing different forms of the sensor.
Figure 5:
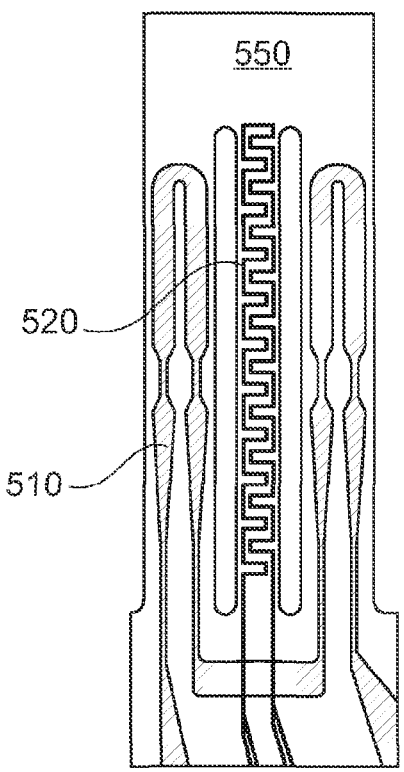

FIGS. 3 to 5 show different embodiments of micro-cantilever based measurement devices according to the invention. As shown in FIG. 3, the micro-actuator fluid property sensor 300 according to embodiments of the invention may comprise an actuating portion (e.g. heater) 310 and integrated sensor 320 separate from the heater, or, as shown in FIG. 4, the micro-actuator fluid property sensor 400 according to embodiments of the invention may comprise a single combined sensor and heater 410. The integrated sensor may be a piezo-resistive sensor operable to detect temperature changes, movement of the micro-actuator, such as bending and flexing, or a combination of movement and temperature.

There may be provided multiple combined heater/sensors, with results taken from each and combined into an averaged overall result, or the like. The fluid medium may be sensed in micro-liter or even sub-micro-liter sized samples. The micro-actuator may sense fluid/coagulate properties using thermal and/or movement based physical property measurements of the fluid medium.

Advantages of the herein described micro-actuator based micro-thermal probe is that because it extends into the fluid medium, there may be lower conduction (heat loss) to the substrate compared to a heater/sensor arrangement that is embedded within or on the substrate (and only of the sensor itself, not the container), and the movement of the sensor means suspensions are circulated, and dynamic reactions maybe sensed better, and/or increased reaction rate thereby providing a fast time to answer.

FIG. 5 shows two suitable alternative arrangements 500, 550 of heater and temperature/movement sensors in the form of micro-cantilevers, both including a heater 510, and a temperature/movement sensor 520, but where the sensor 520 on the left hand version is formed in a serpentine manner along the length of the micro-cantilever, and the sensor 520 on the right hand side has a sensor 520 formed in a serpentine manner along the width of the sensor portion of the micro-cantilever. The different directions of the serpentine formation means the sensors are differently sensitive to longitudinal and linear strain, which may help isolate extraneous strain factors that might otherwise affect the results. For example, using the serpentine sensor on a second micro-cantilever allows that reference beam to be used actively, i.e. it can also be actuated. In the case where both sensors are the same, the actuation of both would cancel out the signal, because one cantilever is located on the positive arm of the Wheatstone bridge and the other is located on the negative arm.

When using a serpentine form of sensor on one of the micro-cantilevers, because the serpentine sensor only measures the thermal change in resistance as opposed to bending, the actuation of both the active and reference micro-cantilevers gives a better purely mechanical signal. For example, in the positive arm (of the Wheatstone bridge) the signal is derived from both the sensed mechanical and thermal properties, whilst in the reference negative arm (of the Wheatstone bridge) it is only thermal properties that are sensed. Thus, using a serpentine sensor configuration may provide the advantages of 1) better isolation of mechanical and thermal signals, and 2) more chaotic mixing due to the movements of both micro-cantilevers. Furthermore, one micro-cantilever may be placed at a different orientation or position to the other micro-cantilever to further improve the mixing characteristics. Moreover, because the thermal portion of the sensor output signals should cancel out when using differently configured sensors, such as the serpentine configurations, the test may be carried out at any pulse length, i.e. the actuation pulse may be longer and therefore have more sweep and mixing effect.

The micro-actuator sensor according to embodiments of the invention may be dynamic, in that it able to be truly extended into the fluid medium, and may provide large sweeping motion(s) to speed kinetics of a fluid medium reaction(s) and keep complex suspensions (e.g. cells, beads, particles, and the like) from settling, as would occur in known prior art passive/static devices 100 in short times (i.e. <30 seconds) where the fluid is static and held in a low volume (i.e. <1 micro-liter) chamber.

Figure 6:
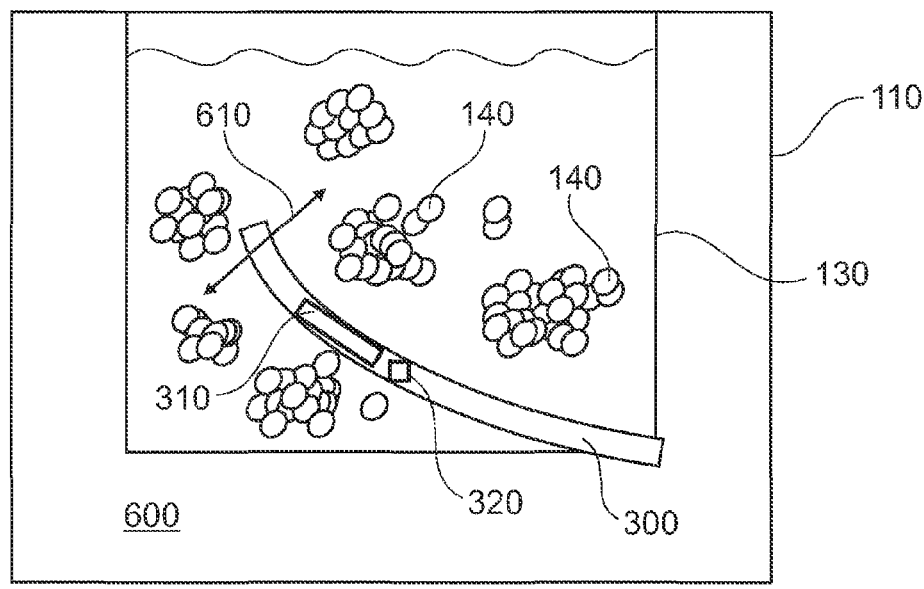
FIG. 6 shows a side view of the micro-actuator based sensor according to FIG. 3, in use.

FIG. 6 shows the dynamic nature of the micro-actuator based sensing system 600 according to embodiments of the present invention. In particular, how the micro-actuator 300 sweeps through a volume of the fluid medium 610 under control of heater 310 and sensing of temperature/movement sensor 320, and helps mix/agitate the fluid medium 130 including binding portions 140. The micro scale heater 310 and sensor 320 are embedded in the micro-cantilever that extends into the fluid. The heater may be pulsed to provide the heat source for measurement and to circulate and accelerate the antigen antibody interaction. Note, FIG. 6 is a view of the sensor taken by bisecting the sensor across the line A to A' in FIG. 3.

Figure 7:
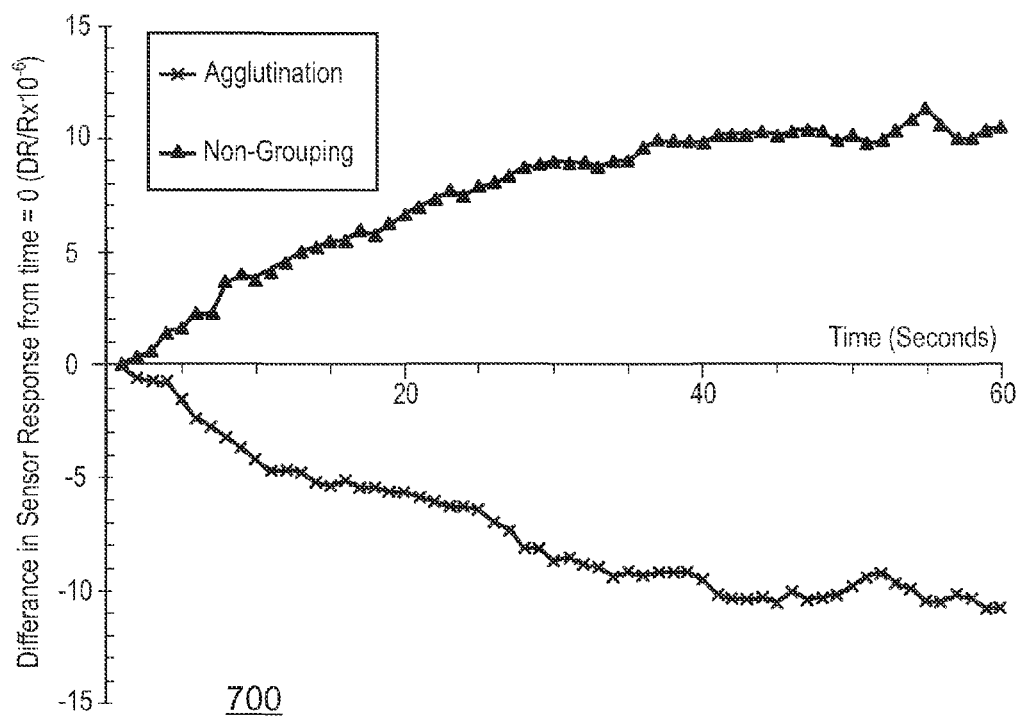
FIG. 7 shows an output graph of the micro-actuator based sensor according to FIG. 6, showing different outputs for different sensed events within the fluid medium sample under test.

FIG. 7 shows a comparison of the micro-actuator sensor response between a non-grouping/binding (i.e. non-agglutination) type fluid medium response versus a grouping/binding (i.e. an agglutination) type fluid medium response, which clearly shows the capability of the micro-actuator based sensor system 600 according to embodiments of the invention to distinguish between different antigen-antibody interactions. In particular, FIG. 7 shows the Peak Height Response of a pulsed micro-cantilever sensor during agglutination of red cells and when no interaction occurs. The non-grouping signature is the effective baseline of a micro-cantilever immersed in a fluid medium, and tends towards a level (upwards to approx+10 on the Y-axis scale of FIG. 7) due to mechanical and thermal settling. The agglutination of red cells shows a fall in the peak height (downwards to approx −10 on the Y-axis of FIG. 7), which indicates there is more thermal diffusion occurring in the agglutinated fluid medium, hence causing increased damping of the micro-cantilever deflections. This may form the basic qualitative "yes/no" type sensor. The "Rate" and "Magnitude" of the response is dependent on the kinetics of the particular antibody-antigen reaction under test, or the like, and can be used to quantify the reaction The coupling of thermal properties of the fluid medium sample under test to the micro-cantilever response may be made by at least the following two means. Firstly, as an indirect thermal response—because joule heating generated from the heater integrated into the micro-cantilever is lost to the surrounding fluid medium through thermal diffusion, convection, and the like, while the remaining heat retained within the micro-cantilever increases the temperature of the sensor. Secondly, as an indirect mechanical response, because deflection of the micro-cantilever may be coupled to the temperature of the device, which may in turn, be coupled to the thermal diffusion, and the like, of the fluid medium sample. The measurements described indicate the potential for use in identification and monitoring of biological and chemical reactions based on thermal properties of the fluid medium sample under test. A method and apparatus to monitor reactions using a thermal signature is therefore provided. The thermal diffusion of heat in a fluid under test is often linked to the weight and size of molecular chains suspended in the fluid, especially those in proximity to the sensor. The thermal diffusion of heat in a fluid may also be dependent on the volume, mass, and density of suspensions and therefore the heat capacity or volumetric heat capacity of suspensions. The thermal conductivity may proportionally increase to the square-root of molecular weight e.g. during polymerisation of cross-linked network structures which, after longer times, may decrease upon structural relaxation.

FIG. 8 shows a more discerning agglutination response. In particular, it shows a typical inverted amplitude output of a II-type (i.e. single integrated heater/temperature sensor) micro-cantilever sensor over time for a group A blood, Antibody B agglutination test. The sensor output response clearly indicates the points in time of: addition of sample 801, spiking with agent 802 and the agglutination reaction taking place 803. Mixing is provided on-line by the micro-cantilever movement during use. The response amplitude values are plotted over time, recording the output of the sensor at a fixed time after each actuation pulse (e.g. 50 ms or 100 ms or 200 ms, etc. after the start of the pulse).

In Newtonian and non-changing-over-time fluids, the plotted amplitudes should not change once the fluid is settled (i.e. in a steady state) over the micro-cantilever(s) (at the vertical line along the x-axis). Similarly, as soon as the changes due to the addition of another fluid/reagent are settled, a higher (in this example) equilibrium is reached and the response reaches another second plateau. Thus, it can be seen that the presence of the immunoassay (i.e. antigen-antibody) reaction and resultant induced agglutination and/or aggregation and/or other related effects in the sample, changes the sensor response. With careful calibration, this allows the sensor to detect the presence of, and extent of, any desirable fluid medium reaction, such as agglutination of blood.

FIG. 9 shows a similar typical inverted amplitude output of a II-type (i.e. single heater/temperature sensor) sensor over time for another agglutination type test (using a commercially available spiking agent, Omega 25M). The sensor output response again clearly indicates the points in time of: the addition of sample 901 the spiking with reagent 902 (at the vertical line) and the particular reaction taking place 903. Again, mixing is provided on-line by the micro-cantilever movement during the test.

In the tests of FIGS. 8 and 9, the spiking of the sample is done a predetermined time after the sample has been initially added to the test system fluid reservoir. This is done so that the sample reaches thermal equilibrium (e.g. reaches a stable ambient temperature), which can be sensed by the sensor and calibrated against. All the readings are taken during actuation of the micro-cantilevers, approx 100 ms after the rising edge of the driving signal/pulse. The exact timings may be varied according to the characteristics of the sample under test, or ambient conditions. In any case, preferably, localised thermal equilibrium should be reached within each pulse. The values on each of the Y-axes corresponds to changes in the thermal properties of the spiked sample. The micro-cantilevers may be repeatedly pulsed during operation.

Another suitable calibration test comprises using the micro-cantilever Fluid Probe in Glycerol/water mixtures. These may then be used in conjunction with previous characterisation tests in air, for example using 10 mW and 100 ms pulses that indicated that a thermal component of the micro-cantilever response is present and this has been referred to as thermal signal. The piezo-resistor response may be dependent on rheological and thermal properties of the fluid medium under test, such as the thermal conduction and heat capacity. Furthermore, the heat convection coefficient from the surface of the micro-cantilever to air may be up to approximately 40 times less than water, and therefore heat is maintained in the micro-cantilever, giving higher temperatures and hence a higher overall response in terms of thermal signal and mechanical deflection. Testing in glycerol solutions with known rheological and thermal properties allows the particular micro-cantilever's mechanical and thermal response to be studied, characterised, and ultimately removed from test results, to thereby provide a modified response based on the properties of the fluid medium under test only.

Since production of the micro-cantilevers is highly uniform, calibration of a sample of the micro-cantilevers from a production run (e.g. a wafer) may be used to characterise all the micro-cantilevers in the same production run. The micro-cantilever response characteristics may then be saved, for example in a memory operably coupled to the sampling circuitry, for reference when providing fluid medium sample test results in the field.

Table 1 gives the approximate rheological properties and thermal conductivity of air and standard percentage weight glycerol mixture solutions with respect to water at 20° C., noting that the specific heat capacity of air is 1.01 $J \cdot g^{-1} \cdot K^{-1}$ and the range of heat capacities of the water-glycerol mixture solutions is 4.18 to 12.14 $J \cdot g^{-1} \cdot K^{-1}$ at 20° C., with pure water having the lowest value:

TABLE 1

| Fluid | Viscosity (cP) | Density ($g \cdot cm^{-3}$) | Thermal Conductivity ($W \cdot m^{-1} \cdot K^{-1}$) |
| --- | --- | --- | --- |
| Air | 0.019 | 0.00008 | 0.025 |
| 0% Glycerol | 1.005 | 0.99823 | 0.591 |
| 30% Glycerol | 2.50 | 1.07270 | 0.482 |
| 70% Glycerol | 22.5 | 1.18125 | 0.352 |
| 80% Glycerol | 60.1 | 1.20850 | 0.327 |
| 99% Glycerol | 1150 | 1.25850 | 0.284 |

The micro-actuator sensor measurement may be performed using a calibrated electronics interface, for example a balanced Wheatstone diode bridge circuit. The actuation heat pulse(s) is controlled from a function generator and connected through the electronics interface. The electronics is controlled through software, e.g. over a Serial Peripheral Interface (SPI) bus interface with digital gain/channel selector, and the integrated temperature/movement sensor response is recorded, for example through a triggered data acquisition process on a single analog channel. The diode bridge output may be routed through a shielded BNC connector block to connect to a data acquisition device. The acquisition device may have, for example, a resolution of 16-bits and a sampling rate set at 100 KS/s, thereby giving 10 µs resolution, however any suitable sampling rate and resolution may be used and the invention is not so limited. In the example shown, the measurement limits are set to 1V to improve resolution of measurement, with a fixed gain applied to scale the output of the balanced Wheatstone bridge, and the total number of samples may be 5000. Each sample may be saved as, for example, a 6 decimal place double precision integer. In practice, the balanced Wheatstone bridge output may not in fact be zero, but slightly offset. When this is amplified, the baseline output voltage of the balanced Wheatstone bridge can be a few mV above zero. Also, the baseline can change over time when using a quarter bridge circuit due to the temperature of the solution with respect to the micro-cantilever. However, this baseline drift does not affect the absolute change in voltage signal due to a change in resistance (due to temperate or movement of the micro-cantilever device) and therefore each actuation event can be shifted to zero to allow a comparison between micro-cantilever devices. Each device may be potted with a silicone sealant around the micro-cantilevers to stop the fluid medium under test from contacting the electrical contact pads to the heater and/or sensors respectively.

Figure 10:
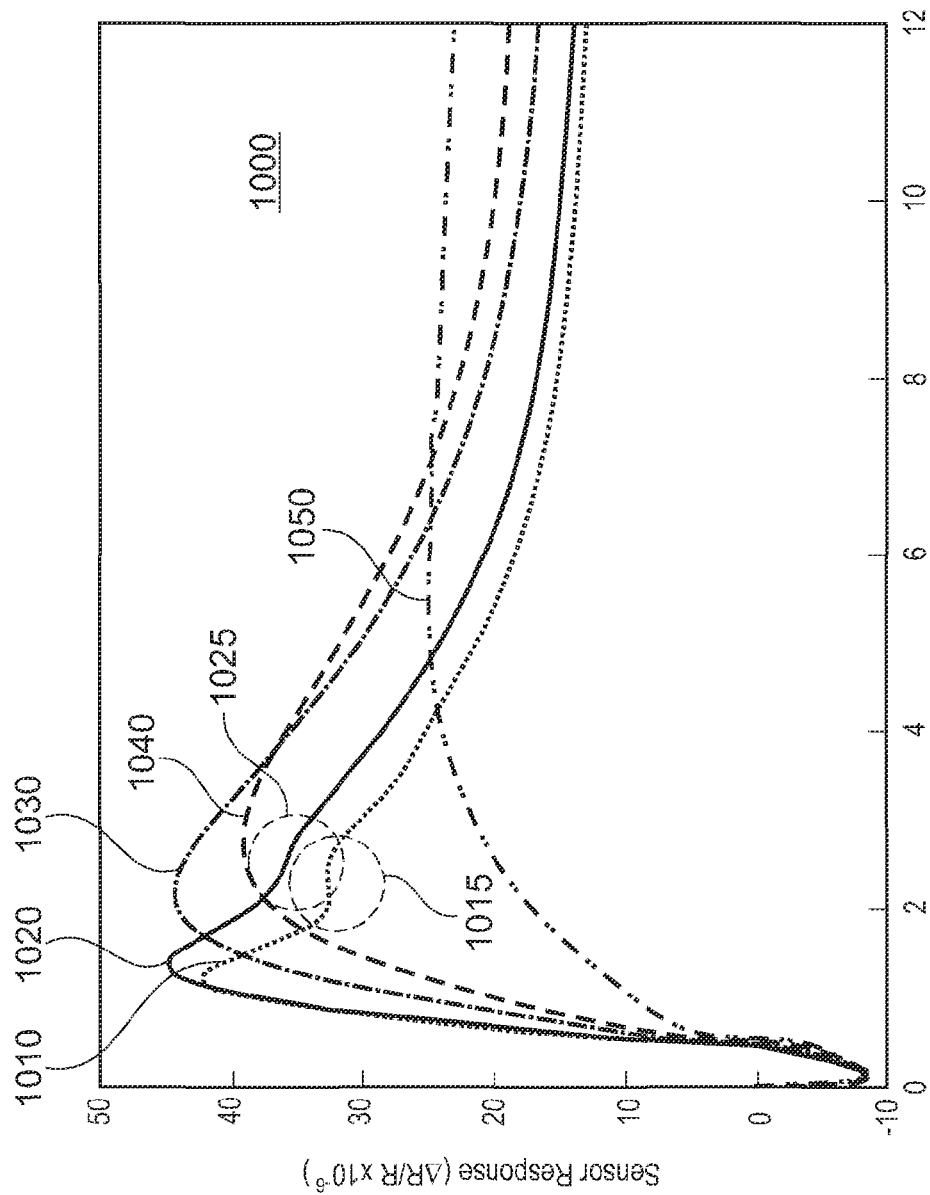
FIG. 10 shows five superimposed output signals from a micro-cantilever sensor according to an embodiment of the invention for a first specified test.

FIG. 10 shows the response of a single exemplary micro-cantilever device in 0 to 99 percentage weight glycerol with respect to water solutions (as described in more detail in Table 1). In this example, the actuation pulse has a 1 Hz frequency and energy of 90 µJ. The micro-cantilever device is chemically treated and dried between tests to prevent cross contamination of the fluid mediums under test. The plot shows measurements at 0% (red, 1010), 30% (blue, 1020), 70% (green, 1030), 80% (orange, 1040), and 99% (purple, 1050), concentrations. Error bars of the micro-cantilever response in pure water are <1% and therefore have not been shown.

The response of the micro-cantilever in the lowest viscosity solution (0 wt %, 1010) shows an overshoot peak and secondary oscillation 1015 which is a mechanical artefact. In the next solution (30 wt %, 1020) the secondary oscillation 1025 is damped and the peak has moved to the right along the x-axis, i.e. it has occurred later in time. This is expected if the response is a mechanical artefact, because the micro-cantilever will move less through the fluid and at a slower rate. The peak height is also expected to be reduced though this is not measured in this example. As the response also has a thermal component/artefact, the lower thermal conductivity of the 30 wt % glycerol implies more heat is being retained in the micro-cantilever (because the heat is not being transferred to the surrounding fluid medium so well), therefore inducing a higher thermal signal on the integrated temperature/movement sensor. Measurements in higher wt % glycerol solutions (1030-1050) have no distinguishable secondary oscillation and the peak height falls and moves further right along the x-axis, although thermal conduction of the fluid medium continues to decrease. This trend may be due to the rheological properties increasing substantially (viscosity increases from 2.5 cP to 1150 cP) from 30 wt % to 99 wt % glycerol, while thermal conduction falls by approximately half.

The above-described micro-actuator, in particular micro-cantilever, sensor system, is operable to measure specific antigen-antibody interactions/reactions by using the thermal signature. It has been tested using agglutination of red blood cells, and in a normal control test. For example, an Anti-A test may be conducted with 20 Mitres of Type A whole blood at 40% haematocrit using anti-A antibody. The micro-cantilever(s) used are each electrically isolated from the fluid medium using non-conductive silicone rubber to insulate electrical pads and connections. The micro-cantilever(s) may be connected in a quarter bridge configuration with only one device actuated. The micro-cantilever may be sampled at 100 KS/s and voltage measurement limits set to +/−1 Volt. The micro-cantilever may be pulsed at 1 Hz and data is analysed for peak height and peak position. The result may have a rolling average, for example of 10 samples, applied to the data to provide averaged results.

Whilst the micro-cantilever sensor according to embodiments of the invention may benefit from suitable calibration, to allow quantitative measurements to be taken, the qualitative measurement (i.e. YES/NO) are more easily achievable. This is because, if it is known there is an antigen-antibody reaction, such as agglutination, reaction occurring (which, for a specified test, such as blood test for a particular antibody presence will be known), as shown in FIG. 7, the micro-cantilever sensor system provides positive results that trend in the opposite direction compared to the negative results.

Test measurements shows that the micro-cantilever may be used for specified antigen antibody interaction measurements, because the thermal response increases where the binding does not occur and decreases where it does occur. This therefore provides an immediate observable/detectable differentiation between the two cases, and further, a very fast time to answer.

The micro-cantilever sensor may be further arranged to provide for multi-parameter sensing (mechanical and thermal) or a thermal sensor that has unique attributes e.g. enhanced mixing (through increased or specific forms of sweep motion).

Design of a Thermal Sensing Probe and Comparison to Standard Technique

As shown in FIGS. 1 and 2, the standard method for measuring the thermal conductivity of a fluid is to use a hot wire method. The method is based on the measured dynamic rise in temperature a known distance from a linear heat source through a test fluid medium near a surface where the heater and temperature sensor are located. A similar arrangement can be used in a fluid flow, where a known flow carries the heat to the sensor and a measurement of the temperature is made. The heater and sensor are both simple metalized tracks acting as a joule heater and thermocouple respectively.

In comparison, the micro-cantilever fluid probe according to embodiments of the invention also includes heaters (that may be formed from metallization), but now further includes a metal piezo-resistive temperature and movement sensor.

The conventional method has many limitations. Firstly the heater and sensor are fabricated on the surface of the substrate with a thin electrical insulation layer. As the substrate will provide an excellent thermal conduction path the measurement is both dependent on the substrate, and requires high power to compensate for power loss to the substrate. Whereas, the freely moving micro-cantilever according to embodiments of the invention may extend into the sample, thereby having a lower conduction heat loss to the substrate and therefore improves these aspects.

The conventional technique is also static on the surface and therefore is truly measuring the boundary close to the substrate. For example, if the sample has suspensions these would settle on the substrate surface and dominate the measurement (for example, this can happen in short times (i.e. <30 seconds) where the fluid is static and held in a low volume (i.e. <1 micro-liter) chamber. Whereas, the micro-cantilever is extended into the fluid allowing a volume measurement and can also keep particles suspended using the dynamic actuation of the beam. In reaction measurements, this dynamic actuation is particularly advantageous, because it can also accelerate mixing for fast time to answer.

As the micro-cantilever is an extension into the fluid, and has lower dependence on the substrate, the device will be able to make more sensitive measurements of the fluid medium sample under test, and reactions occurring therein.

The micro-cantilever sensor system according to embodiments of the invention may be fabricated to bury the heater and sensor layer at the interface of the bi-morph materials forming the micro-cantilever, so they are located as close to the neutral axis as possible. This allows the micro-cantilever to be used for dynamic mixing, but have near zero mechanical signal on the integrated piezo-resistor. This therefore allows better thermal and movement separation of the integrated sensor output.

The piezo-resistor may be formed from a suitable material, such as CuNi, Gold, Aluminium or Platinum, with the particular choice of metal/alloy dependent on the required thermal sensitivity (relatively higher or lower). CuNi has low temperature coefficient of resistance and therefore has lower sensitivity to changes in temperature due to thermal changes in the fluid. Gold, Aluminium and Platinum have high temperature coefficient of resistance and therefore have higher sensitivity. Suitable choice of metal for the sensor may also allow the heater and sensor layer to be realized together, for example because Gold and Platinum are also suitable materials for heaters.

Design of a Multiparameter Fluid Probe

It is also possible to combine a mechanical (viscosity) micro-cantilever fluid probe with a thermal measurement. Such a system may be arranged so that in a single low energy pulse, it is possible to be able to extract measurements for multiple characteristics of a fluid medium, including but not limited to: viscosity, thermal conductivity, heat capacity, density, and temperature. This may be provided by selecting a piezo-resistor material which gives a response that is 50% sensitive to deflection and 50% sensitive to temperature. E.g. NiChrome would be suitable choice.

The micro-actuator sensor is capable of measuring specific antigen antibody interactions using changes in physical properties of the fluid medium, such as mechanical damping on the micro-cantilever sweeping, and, where the micro-actuator is activated through application of heat, from the thermal diffusion of heat away from the energised micro-cantilever into the fluid medium.

The micro-actuator sensor may measure in a mechanical mode, a thermal mode, or a combined mechanical and thermal mode. The different combinations may provide multi-parameter feedback and secondary confirmation of the specific antigen antibody interaction. Additionally, or alternatively, multiple parameter measurement may also be realised though using multiple micro-actuators, each set into a different and independent mode of operation.

The micro-cantilever sensor may be based on a thermal bimorph or thermal multi-morph micro-actuator using two or more layers of material having dissimilar coefficients of thermal expansion. The thermal morphing may be operated by using an integrated metal heater and piezo-resistive sensor. The heater may be separate to the sensor, or a combined heater/sensor may be used instead. Using multiple layers of material may provide truly out of plane deflection, which allows interaction and measurement/feedback of environmental parameters in a fluid medium.

The micro-cantilever may be formed in micro dimensions, for example, having a length of 600 to 800 microns, a width of 80 to 300 microns, the combination of which providing a 200-400 microns tip deflection. The micro-cantilever so formed may allow interrogation of micro-liter sample volumes of the fluid medium.

In a mechanical sensing mode, the micro-cantilever is pulsed with a short electrical signal through integrated heaters (formed of a suitable material, such as platinum, gold, aluminium, or any other suitable metal or alloy) which causes a sweeping due to dissimilar thermal expansion of the two or more layers having dissimilar coefficients of thermal expansion forming the micro-cantilever. The resulting deflection is governed by physical properties of micro-cantilever, and the (potentially changing) properties of the fluid medium being sensed. Since the properties of the micro-cantilever are known, and/or may be calibrated against different known mediums (having known properties, or changes to properties), a sensor method and apparatus may be provided that can sense unknown fluid mediums, or fluid mediums having unknown reactions occurring, in order to characterise and measure the fluid medium reactions, such as specific antigen antibody reactions, more particularly agglutination, and blood clotting type reactions.

The different fluid medium properties that may be sensed include, but are not limited to: viscosity, density, viscoelasticity, yield stress, and/or effects of aggregation or sedimentation of suspended particles or cells. Since the sensor is dynamic, the sensing of the fluid medium characteristics are not extremely localised, which is an important benefit when measuring changes in a fluid medium (especially due to chemical or biological reactions), as they operate over a volume of space, rather than at a single point.

When activating the micro-cantilever through application of heat, this may be carried out by providing a known form of electrical pulse to the heater. The electrical pulse width applied to the heater may be set for optimum detection operation based on the known physical properties of the fluid medium being tested, or on the particular known physical property being measured. A typical useful range of pulse length is up to 5 ms.

| Type of Measurement | Typical Pulse Width | Typical Peak Power | Typical Average Power | Typical Pulse Energy |
|---|---|---|---|---|
| Combined Thermal and Mechanical | 1-5 ms | 100-500 mW | 10-50 mW | 0.1-2.5 mJ |

When attempting to detect changes to fluid medium properties for a specified antigen-antibody reaction, on specific binding of the requisite antigen antibody interactions, the mechanical signal of the micro-cantilever may be damped, and so decreases in amplitude and/or number. The damping may therefore shift the time taken to reach maximum amplitude to higher values, and/or may reduce signal height. The damping effect may be enhanced by using beads with coated antibodies in the reaction. These beads may be formed on the micro-cantilever in a suitable way, thereby ensuring the reaction operates within the area surrounding the micro-cantilever, or thereby turning the sensor into the catalyst for the reaction to occur. This is particularly useful when using the micro-cantilever as a diagnostic sensing device in chemical, biological (especially health-based biological testing reactions—such as blood sampling), or for testing the outcome or on going status of industrial chemical/biological processes, or any other catalyst driven process sampling scenarios.

The mechanical signal damping of a micro-cantilever according to the invention may be enhanced using a paddle formed on or as part of the micro-cantilever, as slits or holes in the micro-cantilever or paddle, or by forming the micro-cantilever in such as way during construction (e.g. by molding and/or by using planar construction techniques). The paddle may also increase reactionary area, sensing area, or both. The slits or holes (i.e. perforations) may be formed so that they intentionally capture larger bound suspensions (such as coated beads) and therefore restrict flow through the beam, or the perforations may be formed to only selectively capture certain particle types or sizes in the fluid medium. Where a fluid medium reaction being sensed creates particles that increase with size over time, for example as part of an antigen-antibody binding, the perforation may be formed to interact with the fluid medium reaction at a certain, significant point in time (based on size of particles now existing). In this way, the status of a fluid medium reaction may be determined with more accuracy.

In a mechanical sensing mode it is advantageous to have a low temperature coefficient of resistance for the movement sensing piezo-resistor (e.g. by forming it from a material, such as Constantan—CuNi). In this way, the movement signal due to mechanical deformation may be maximised. It may also be advantageous to place the piezo-electric sensor close to the surface of the micro-cantilever, and/or away from the neutral axis of the overall micro-cantilever device, in order to increase stress/strain experienced by the piezo-electric sensor upon bending of the micro-cantilever.

In a thermal sensing mode, the micro-cantilever may be pulsed with a longer electrical pulse than used with the mechanical only sensing mode. This may be done to either energise the cantilever into a steady state (e.g. by using >50 ms pulse width) within the fluid medium, or to deliver a defined 'packet of energy', i.e. thermal energy impulse, to dissipate into the surrounding fluid medium. Any reduction in deflection of the heated activated micro-cantilever as this heat energy dissipates into the fluid medium may then characterise, or help to characterise, the fluid medium reaction. If the fluid medium has a higher thermal diffusivity, more of the energy is diffused into the fluid medium, and so less heat energy remains in the micro-cantilever to heat the micro-cantilever structure, causing an increase in temperature of the fluid medium.

The rate and absolute change of the temperature of the micro-cantilever can be used to indicate the thermal properties of the medium, such as but not limited to the thermal conductivity, heat capacity, and combined factors including the thermal diffusivity and volumetric heat capacity. The heat transfer rate between the micro-cantilever surface and fluid medium sample may also provide an indication of other parameters, such as the heat convection coefficient. The rate and absolute change in temperature of the micro-cantilever can be measured directly from the integrated metal piezo-resistor, which will have an associated (and predetermined) temperature sensitivity. Upon specific antigen antibody interactions occurring, the thermal diffusion of the localised fluid medium may change. For example, it may increase, thereby reducing the energy remaining in the micro-cantilever during each pulse, which lowers the temperature/signal on the micro-cantilever sensor, thereby indicating the presence of that specific antibody-antigen interaction, when the micro-cantilever is suitable calibrated.

The thermal sensing mode may also provide enhanced operation, because the longer pulse width allows larger sweep of the medium, thereby increasing the mixing dynamic and hence reaction rates.

In a thermal sensing mode, it may be desirable to have a sensor with high temperature coefficient of resistance, such as gold or platinum. In such a configuration, it may also be advantageous that the heater and sensor are of the same material, such that that can be deposited in a single layer during fabrication. It may be advantageous to place the sensor close to the neutral axis of the overall micro-cantilever, such that the stress is zero upon bending. The sensor may be formed in a serpentine configuration to reduce mechanical response along the length of the cantilever. For a two layer micro-cantilever formed of two layers having different coefficients of thermal expansion, with an integrated heater and sensor layer, the micro-cantilever may be engineered such that the optimum deflection is achieved while the sensor is located at the neutral axis when the thickness of the top layer $t_1$ and the thickness of the bottom layer $t_2$ are:

$$t_1 = \left( \frac{kL^3}{E_1 w_1 + (E_1 w_1)^{3/2} (E_2 w_2)^{-1/2}} \right)^{1/3} \text{ and } t_2 = t_1 \sqrt{E_1 w_1 / E_2 w_2}$$

where:

k is the desired stiffness of the micro-cantilever beam, L is the length of the micro-cantilever beam, $E_1$ and $w_1$ are the Young's modulus and width of the top layer, $E_2$ and $w_2$ are the Young's modulus and width of the bottom layer.

The micro-cantilever sensor layer may be sensitive to movement, such as bending, or temperature of the sensor, or any other suitable change in physical parameter of the micro-cantilever, thereby indicative of the movement or temperature of the micro-cantilever as a whole. The movement or temperature of the micro-cantilever as a whole may then be used to determine a characteristic of the fluid medium, and its reactions.

The micro-cantilever sensor may also be used in a dual movement and thermal sensing mode, whereby short(er) and then long(er) pulses (or the opposite) are alternatively used to measure mechanical and thermal response in turn, or in a combined mode, whereby a sensor which is both mechanically and thermally sensitive (for example, when formed of NiChrome) is used and the thermal and mechanical properties are extracted from the response. In this case the time of maximum deflection may be indicative of the mechanical response and the amplitude (i.e. height) of maximum response may indicative of the thermal response. The time(s) and or amplitude(s) of secondary deflections may also be used, in a similar fashion. Rate of decay between primary and secondary deflections may be particularly of use in determining a change in physical properties of a reactionary fluid medium being tested, thereby allowing characterisation of the reaction.

The micro-cantilever sensor may also be used to heat the low volume fluid medium sample to a predetermined temperature, by providing a constant DC offset to the electrical pulse to the heater. This may allow a controlled environment thermal range and thermal optimum (i.e. "biasing") for the specific antigen-antibody interaction being sought, or tested. The predetermined temperature, and changes thereto due to the reaction (e.g. if it is exothermic or endothermic), may be measured by the nominal resistance of the piezo-resistor before pulsing or through feedback, e.g. by detecting the heater nominal resistance.

The construction of the micro-cantilever sensors may be chosen to match a particular test case scenario, i.e. to provide suitable broad thermal characteristics of the sensor to match the fluid medium sample being tested. Table 2 below shows the thermal capacity, thermal conductivity and thermal diffusivity of different materials that may be used in the construction of the micro-cantilever sensors:

TABLE 2

| | Thermal Capacity | Thermal Conductivity | Thermal Diffusivity |
|---|---|---|---|
| Gold | 0.5944 [Cal/cm$^3$ · ° C.] | 0.7600 [Cal/s · cm · ° C.] | ~1.293 [cm$^2$/s] |
| Chromium | 0.8783 [Cal/cm$^3$ · ° C.] | 0.2247 [Cal/s · cm · ° C.] | ~0.2558 [cm$^2$/s] |
| Aluminium | 0.5805 [Cal/cm$^3$ · ° C.] | 0.5664 [Cal/s · cm · ° C.] | ~0.9757 [cm$^2$/s] |
| Silicon | 0.3929 [Cal/cm$^3$ · ° C.] | 0.2868 [Cal/s · cm · ° C.] | ~0.73 [cm$^2$/s] |
| Silicon Dioxide | 0.2645 [Cal/cm$^3$ · ° C.] | 0.00238 [Cal/s · cm · ° C.] | ~0.009 [cm$^2$/s] |
| Alumina | 0.0279 [Cal/cm$^3$ · ° C.] | 0.0717 [Cal/s · cm · ° C.] | ~0.084 [cm$^2$/s] |
| Polylmide | 0.4186 [Cal/cm$^3$ · ° C.] | 0.00037 [Cal/s · cm · ° C.] | ~0.00088 [cm$^2$/s] |

From table 2 above, it can be seen that thermal diffusivity of Gold is 3 to 4 orders of magnitude higher than that of polyimide. For simplification, it can be assumed that heaters made of a Gold layer heat up instantly. Based on a simplified transient temperature equation model, it can be assumed that the temperature constant of polyimide cantilever beams that are approximately 6 μm thick and that have the heater buried in the middle, e.g. between layers of differently stressed polyimide, will be in the range of several tens of microseconds.

Comparison of analytical heat diffusion for similar thicknesses of SiO2 membranes using 2nd order partial differential equations for transient temperature in 1-dimension, provides:

$$\frac{\partial T(x, t)}{dt} = D \frac{\partial^2 T(x, t)}{\partial x^2} \text{ and } T(x, t) = T_0 \cdot \left( 1 - erf\left( \frac{x}{2\sqrt{Dt}} \right) \right)$$

Where $T_0$ is the constant temperature at the interface between the heated element and the surrounding medium where x is the distance into the medium, t is the time, D is the thermal diffusivity constant of the medium equal to the thermal conduction divided by heat capacity and mass density, and erf( ) is the Gaussian error function which returns a tabulated value for the argument.

If the distance from the heater is kept at, for example 3 μm, the comparison of Temperature plots using the equation above shows that a polyimide micro-cantilever time constant is several microseconds (up to 0.1 ms). This is some 10× slower than its SiO2 equivalent and some 1000 times slower than the Si equivalent, however it still quick enough such that there is practically an instantaneous heat transfer between the microcantilever and fluid medium. This also shows how much more efficient polyimide cantilevers are (in retaining heat) compared to Si based counterparts—heat 'escapes' from SiO2 based structures approximately 10× faster and from Si-based structures approximately 1000× faster. The above calculations indicate that by having micro-cantilevers actuated by pulses that are 50 ms, 100 ms or 200 ms long, it is possible to apply continuous heating that is 3 orders of magnitude higher than propagation of heat through the polyimide structure. In other words, with each pulse, recording the values after e.g. 100 ms, the micro-cantilever interface with the fluid has definitely reached thermal equilibrium, so that the temperature of the cantilever is at steady state through its volume and the thermal exchange with the fluid is also constant. Therefore the output values are representative of the thermal properties at the cantilever/fluid interface.

Active micro-cantilever sensors according to embodiments of the present invention may therefore allow measurement of a number of different thermal properties of a fluid medium sample, such as any one or more of: thermal conductivity; heat capacity; temperature; volumetric heat capacity; thermal diffusivity, and the like. Furthermore, the monitoring of the (relative) change in these properties and/or rate of change of these properties may be carried out, to aid characterisation of the fluid medium sample, particularly where the fluid medium sample is involved in a reaction, such as agglutination and the like already discussed above.

Thermal Conductivity may be the rate at which heat is transferred by conduction through a unit cross-sectional area of material when a temperature gradient exists perpendicular to the area. The coefficient of thermal conductivity may be expressed as the quantity of heat that passes through a unit cube of the substance in a given unit of time when the difference in temperature of the two faces is 1°. If it is known how temperature sensitive the piezo-resistive sensors inside the micro-cantilevers are, then based on their resistance change (after being de-coupled from the visco-elastic contribution), it is possible to interpret the sensory read-out in the light of said thermal conductivity changes.

Thermal Capacity may be linked to the specific heat of materials (i.e. specific heat*density), and relates to the quantity of heat necessary to produce a unit change of temperature in a unit mass of a substance, or in other words ability of a material to store heat. It has been observed that through aggregation, agglutination, etc. the local density of the fluid medium sample changes. Therefore, monitoring the (relative) change in Thermal capacity (and the rate of change of thermal capacity) from the starting, non-reaction condition can aid characterisation of the fluid medium sample, or reaction occurring.

Thermal Diffusivity describes the rate at which heat is conducted through a medium. It is related to thermal conductivity and thermal capacity (ratio). A high thermal diffusivity inhibits convection.

In more detail, Thermal capacity information will derive from the rate at which the temperature of the fluid medium sample increases and therefore that at which the micro-cantilever response increases. The simple equation is $Q=mc \cdot DT$, where Q is heat transferred, m is mass, c is specific heat capacity, and DT is change in temperature. An extension is to look at this "transient" wise, i.e. using differential equations. So, for example, $dQ/dt=mc\, dT/dt$, i.e. the change in temperature over time of the fluid medium sample is dependent on the power ($dQ/dt$) coming from the micro-cantilever, divided by mass×heat capacity. The mass of the fluid may be unknown, so we can replace mass using density $(p)=mass\ (m)/volume\ (v)$, resulting in $dQ/dt=p\, v\, c\, dT/dt$.

From the above equation, it can be seen that "p c" (density×thermal capacity) is in the characterising equation, and this is the volumetric heat capacity. There is a volume dependency, but this can be overcome by using a known dimension of chamber around the micro-cantilever, resulting in a known volume of fluid medium sample. Accordingly, by definition, if we know certain property values, the rest can be derived. For example, if thermal conductivity is known, and volumetric heat capacity is determined, so can the Thermal Diffusivity.

The micro-actuator sensor according to embodiments of the invention may equally be used for "quantitative" (scaled measure) as well as "qualitative" (i.e. YES/NO) measurements of the specified antigen antibody interactions, or unspecified reactions (to thereby allow specification). For example, the micro-actuator according to embodiments of the invention may allow the categorising of the antigen antibody interactions into several classifications. This is achieved using a self calibration of the micro-actuator sensor through pulsing of the device in known mediums or mixtures thereof, such as air, water, glycol, a specified known antigen-antibody reaction, and the like, and then measuring the relative or absolute change in the deflection signal from the micro-actuator sensor system in those mediums. Subsequent application to unknown mediums or reactions can then produce a characteristic of the unknown fluid medium or reaction, to allow determination of there parameters, including identity.

A second micro-actuator sensor that is not pulsed may be used as a reference in a suitable half or full bridge electronic circuit. This can provide stability by compensating for environment vibrations, background temperature, electrical noise, and the like.

There may also be provided a differential type sensing method that may be applied that uses suitable surface coating of the micro-cantilever sensors (e.g. with suitable antibodies) for testing for things like specified protein-protein bindings. For example, coating the micro-cantilevers with prostate specific antigen (PSA), to aid provide detection of prostate cancer. This sort of method may be used instead of (fluorescence) tagging to measure binding of very low concentrations of proteins, which might not be detectable using the tagging technique. This means earlier detection is possible, which is important for increasing the chance of cure. The disclosed differential sensing method provides the advantages of avoiding changes to the structure of proteins (which occurs when fluorescent tags are applied), and the problem of fluorescent tagging being complex to carry out and difficult to amplify. Moreover, disclosed differential sensing method is easier to multiplex i.e. measure several different markers in one test. For example, a patient presenting with shortness of breath might need up to 5 or more markers tested to confirm the cause. This would be easily achievable by simply coating a suitable number of differential sensors with the requisite antigen, all applied at a similar or the same time, rather than having to run five separate extensive tests using fluorescent tags, which are also not very portable for point of care use.

Moreover, the disclosed differential sensing method is advantageous over resonant silicon and/or passive micro-cantilevers. The problem with resonance (where they are looking for a change in frequency when binding occurs) is that damping in the fluid is significant and it is very difficult to get sharp clear peaks (i.e. the test has a very low Quality-factor), and certainly nothing like the positive YES/NO output achieved by the differential sensing method using an active micro-cantilever disclosed herein. Furthermore, another problem with passive micro-cantilever sensors is the accurate detection of the very small signal deflections (i.e. sub-nm to tens of nanometer) against background environmental drift and vibration that requires a very high resolution deflection measurement that is possibly only achievable with optical interferometer techniques, being both complex and bulky, and requiring controlled conditions (i.e. temperature, vibration).

Figure 11:
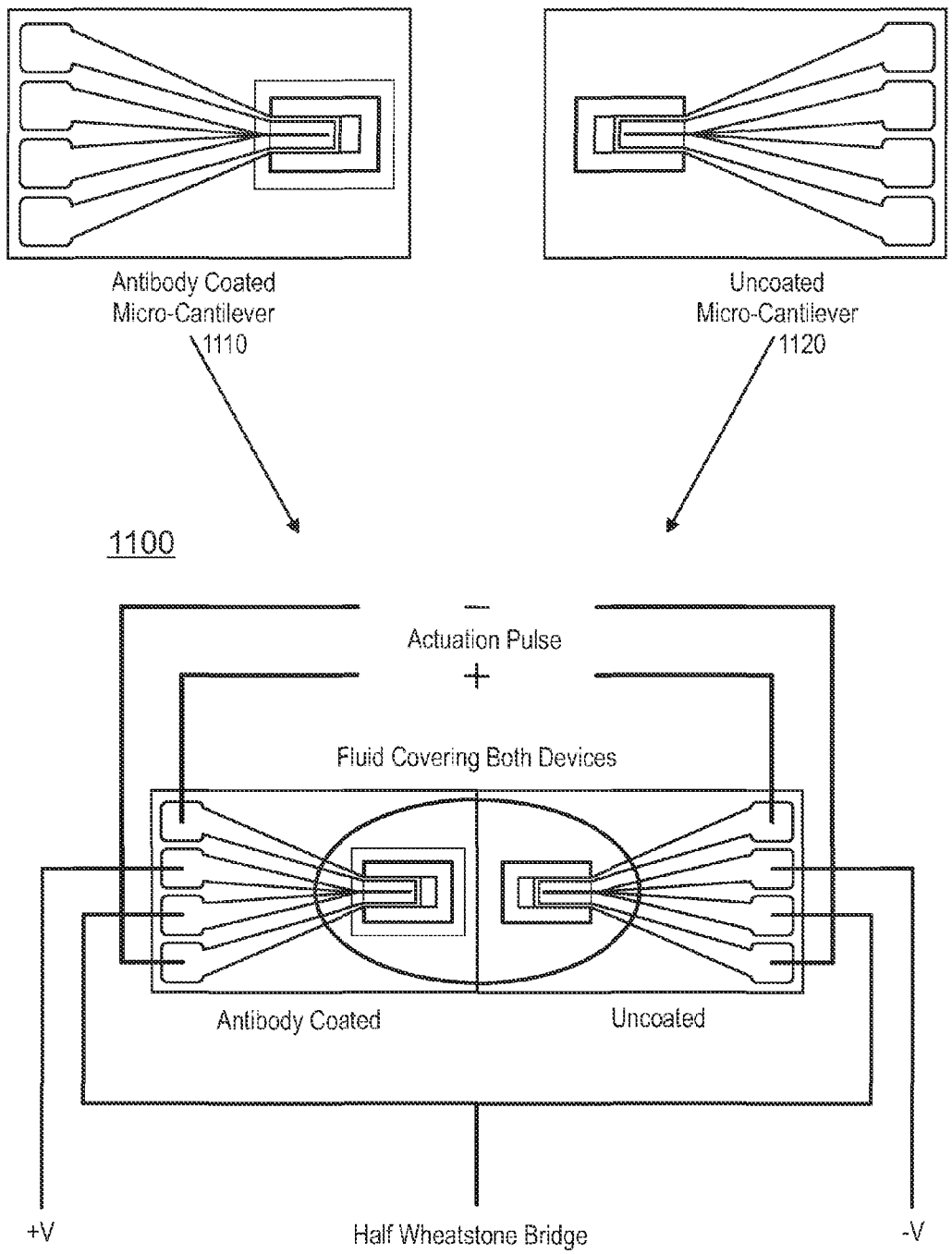
FIG. 11 shows a differential sensing apparatus according to an embodiment of the invention.

FIG. 11 shows an embodiment of the differential sensing apparatus 1100 comprising both an antibody coated micro-cantilever 1110 and an uncoated micro-cantilever 1120. The differential sensing apparatus may be formed by taking one micro-cantilever device and dipping it in a suitable reactive coating and then taking a second micro-cantilever device chip and leaving it uncoated. The two micro-cantilevers can then be positioned with their free ends adjacent or above/below one another, so that the fluid medium sample under test can cover both free, movable ends of the coated and uncoated micro-cantilevers. Both devices are then connected into a Half Wheatstone bridge.

Figure 12:
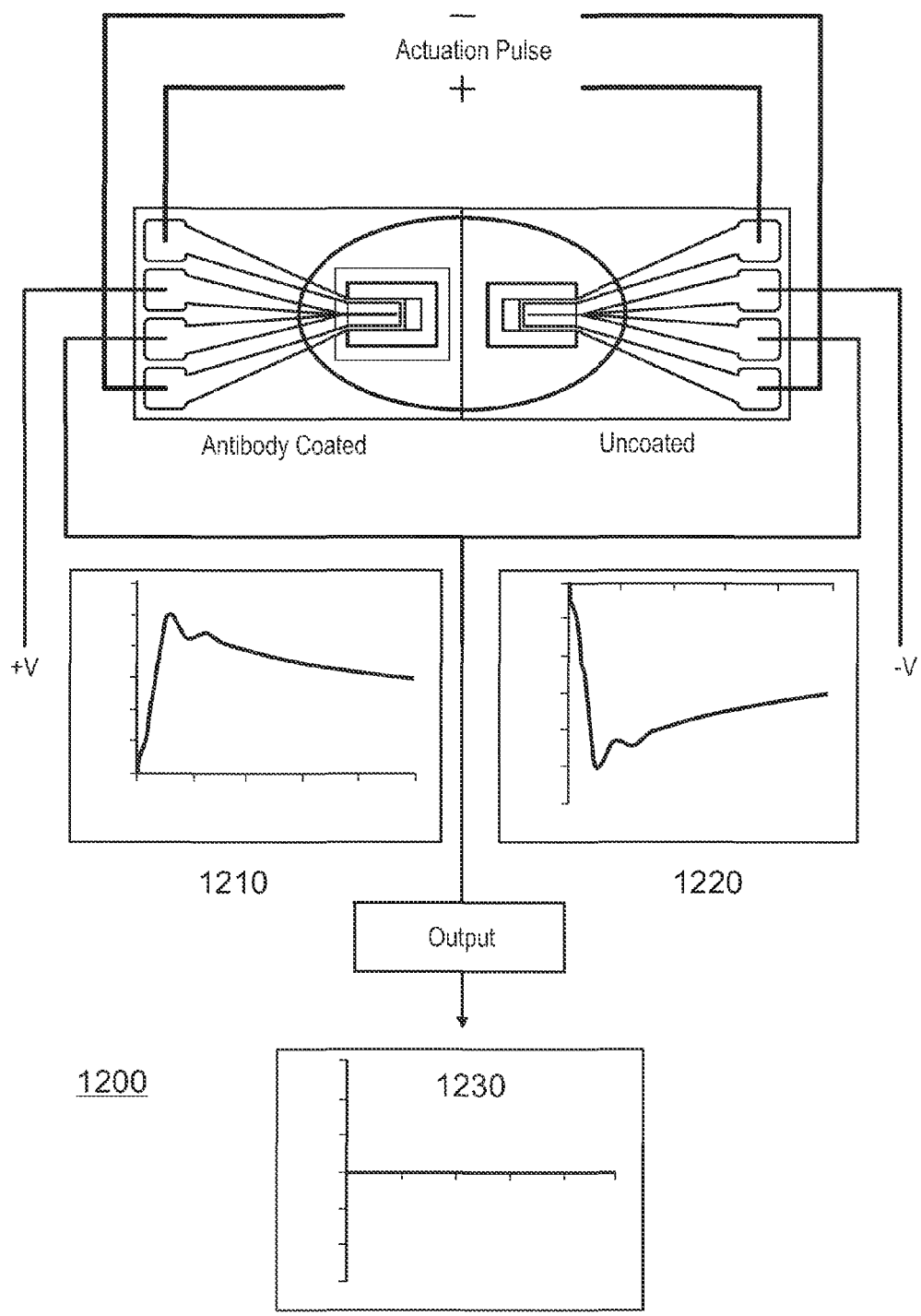
FIG. 12 shows the output of the differential sensing apparatus according to FIG. 11 before agglutination occurs.
Figure 13:
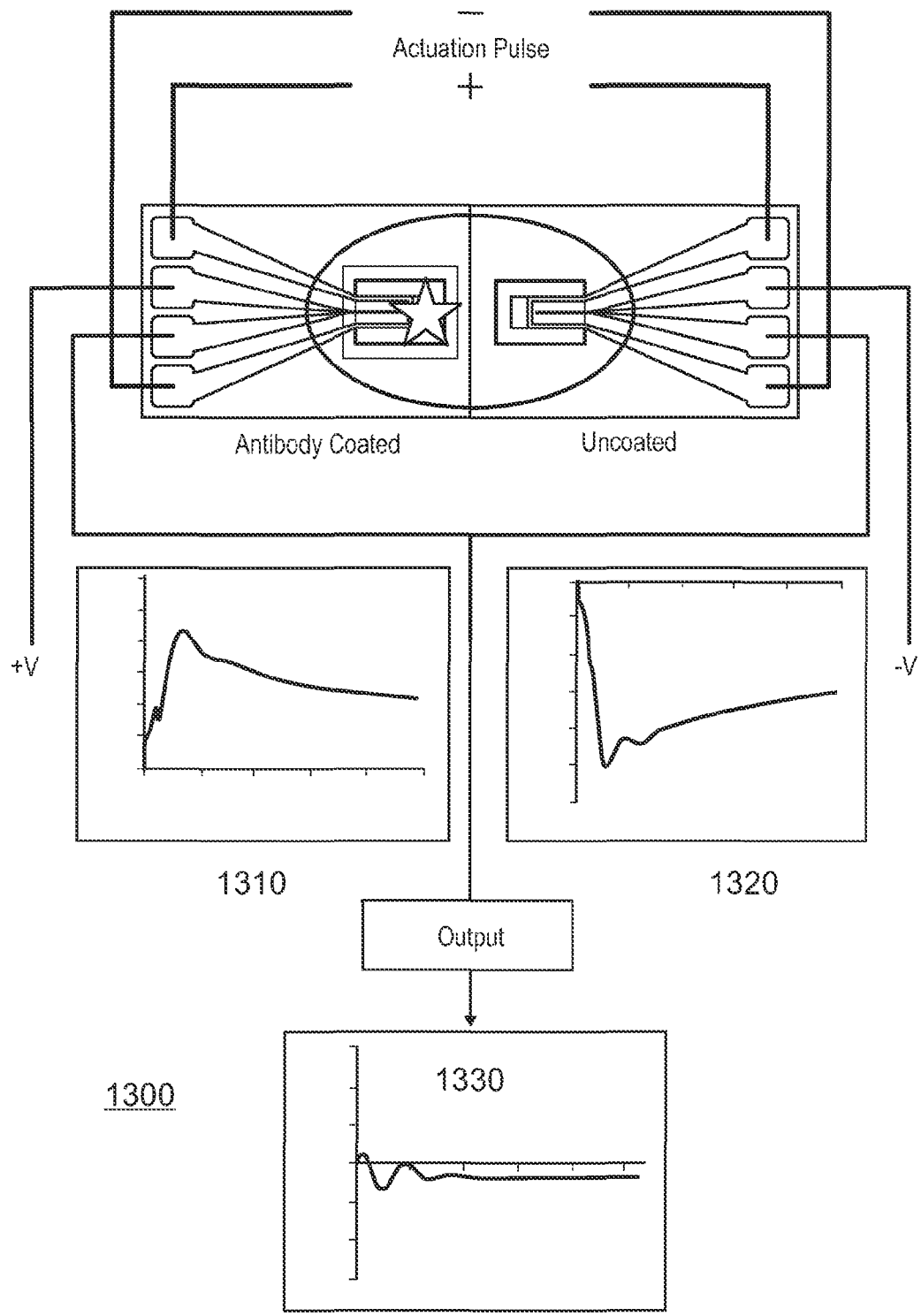
FIG. 13 shows the output of the differential sensing apparatus according to FIG. 11 after agglutination occurs.

A pulsing method may be used to actuate both otherwise identical (apart from the, e.g. antibody, coating on one) micro-cantilevers. The sample to be tested, e.g. blood, is then dispensed over both devices. Initially the response will be approximately the same for both micro-cantilevers, but opposite in polarity (positive 1210 and negative 1220) due to the connection to the half Wheatstone Bridge, and therefore the resultant signal will be approximately a flat zero line 1230, as shown in FIG. 12. Whereas, as a binding happens on the coated micro-cantilever, it changes the physical properties of the cantilever beam and therefore the difference in signal between the coated 1310 and uncoated 1320 starts to change, providing a non-zero output 1330, as shown in FIG. 13. The output signal, being the difference between the two (through action of the Half Wheatstone Bridge circuit), can be massively amplified as the baseline is zero.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures, or parts thereof, cannot be used to advantage.

Unless explicitly stated as being un-combinable, or the combination is physically impossible, the various disclosed and described embodiments of the present invention may be combined, in part or as a whole.

Examples of biasing include: thermal cycling may be used in polymerase chain reaction (PCR) techniques to denature and restructure proteins, which may be achieved by suitable thermal biasing, or desirable chemical phase changes for certain test substance(s) may occur at a certain temperature(s), which can be achieved by biasing (for example liquid to gas, or liquid to solid, e.g. setting of glue). Thermal biasing may also be useful when wanting to read (changes in) physical properties across a temperature range, for example starting at 25° C., through 30° C., to 35° C.

Figure 14:
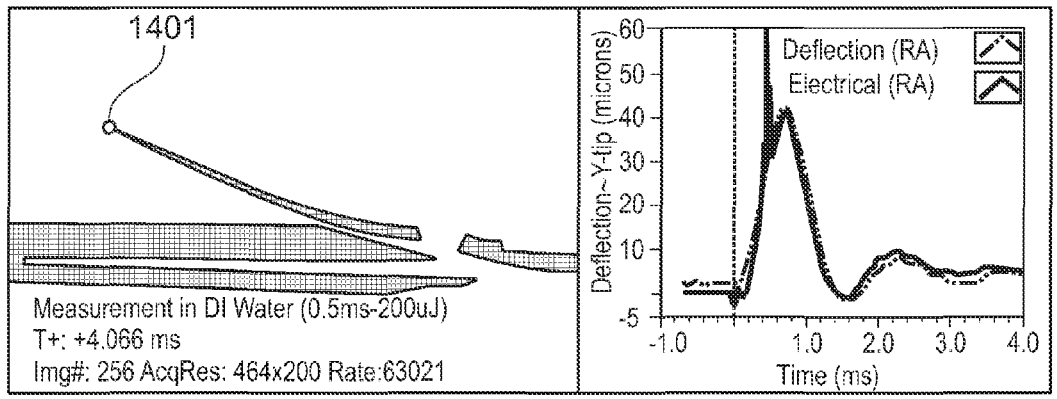
FIG. 14 shows capture of the micro-cantilever tip deflection in deionised Water with the over-laid AC electrical response of the piezo-resistor using a short pulse (0.5 ms)

An embodiment of a short pulse multi-parameter probe is described with reference to FIG. 14, which shows capture of the micro-cantilever tip deflection in deionised Water with the over-laid AC electrical response of the piezo-resistor using a short pulse (0.5 ms). The micro-cantilever motion has been video captured with a high speed camera (63021 fps) and pixels modified to provide a silhouette from which the tip can be tracked (marked by a blue circle, 1401)—this image is shown on the left hand side of FIG. 14. The output signal is on the right hand side of FIG. 14, and this shows how the AC electrical component of the output signal from the piezo-resistor is tracing the mechanical deflection/damping of the signal. The rate of change in deflection, amplitude of deflection, and Position of peak and valley characterise the rheological properties of the fluid.

Figure 15:
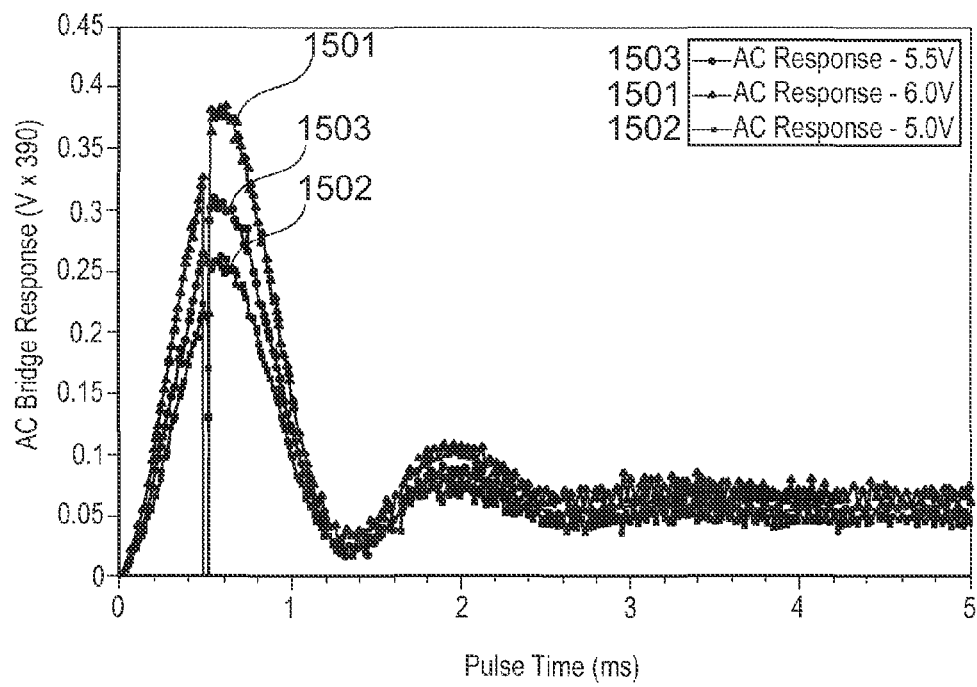
FIG. 15 shows output response for AC (i.e. mechanical only) signals.
Figure 16:
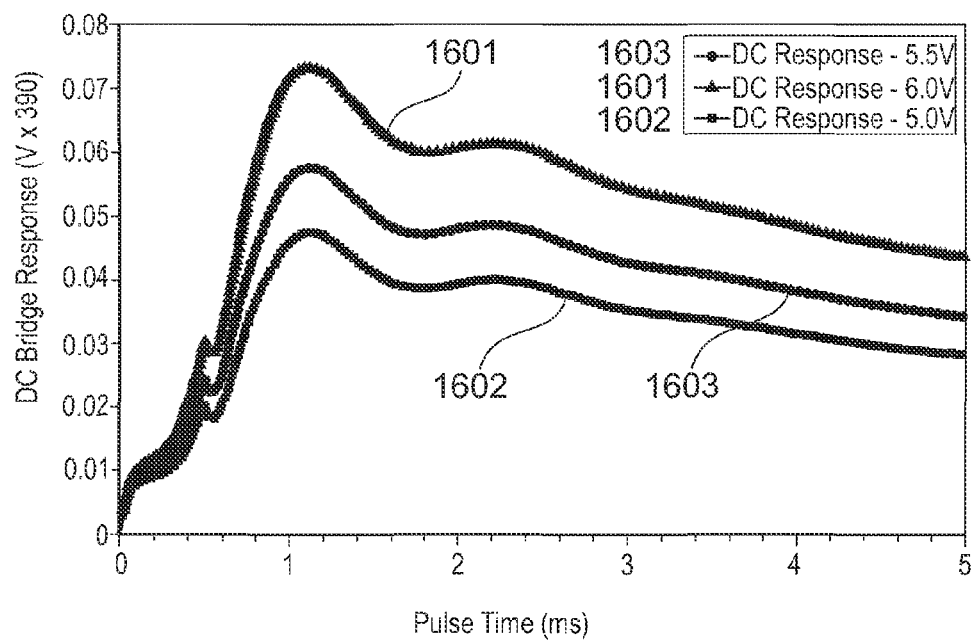
FIG. 16 shows output response for DC (mechanical and thermal) signals.

FIG. 15 shows output response for AC (i.e. mechanical only) signals, and FIG. 16 shows output response for DC (mechanical and thermal) signals. These images show (for pure water, as an example only) how the single response can be decoupled into AC (Mechanical) and DC (Mechanical+Thermal) signals. Both graphs show three actuation voltages (red 1X01, green 1X02 and blue 1X03 on FIGS. 15 and 16, where X is 5 or 6)—i.e. different powers applied to the device micro-cantilevers, by which the micro-cantilever is made to move different distances through the fluid medium sample. In the DC response (i.e. FIG. 16) we see the mechanical oscillation artefact on the micro-cantilever response, but this is on a second thermal signal which includes the cooling at, for example, times >3.5 ms where we see in the AC data (FIG. 15) that the micro-cantilever is at rest.

Figure 17:
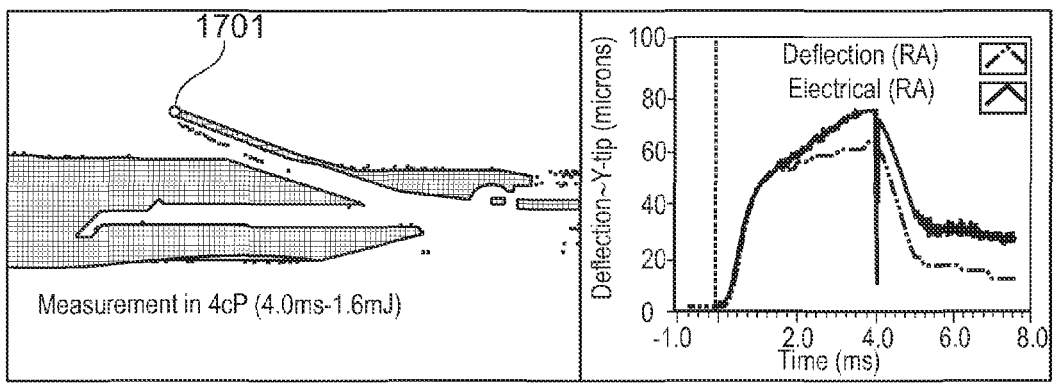
FIG. 17 shows capture of the micro-cantilever tip deflection in a 4 centipoise (cP) glycerol/water mixture with the over-laid AC electrical response of the piezo-resistor using a larger pulse (4.0 ms)

FIG. 17 shows capture of the micro-cantilever tip deflection in a 4 centipoise (cP) glycerol/water mixture with the over-laid AC electrical response of the piezo-resistor using a larger pulse (4.0 ms). The cantilever motion has been video captured with a high speed camera (63021 fps) and pixels modified to provide a silhouette from which the tip can be tracked (marked by a blue circle, 1701)—shown in the left hand side of the figure. This shows how the AC electrical component of the output signal initially traces the mechanical deflection/damping of the signal and then deviates between 1-4 ms. This additional signal is the thermal component of the output signal. The rate of increase and size of increase are characteristic of, for example, the thermal diffusion of the fluid sample.

Figure 18:
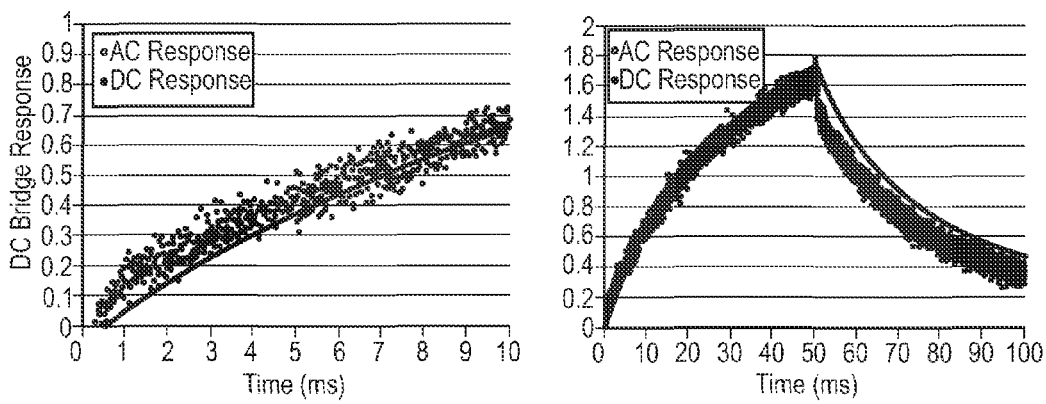
FIG. 18 shows use of the micro-cantilever probe in a Glycerol standard (30% weight with respect to water) with a longer actuation pulse (50 ms pulse width and approximately 2.5 mJ energy), with DC bridge response vs time on the left, and deflection vs time on the right hand side.

FIG. 18 shows use of the micro-cantilever probe in a Glycerol standard (30% weight with respect to water) with a longer actuation pulse (the specific example shown has 50 ms pulse width and approximately 2.5 mJ energy). This figure shows the characteristics can be further extended to longer actuation pulses. A mechanical characteristic is seen to occur as per the high speed camera capture when the pulse is switched on and when it is also switched off. This region could be sampled at higher data collection sampling rates, for example to provide greater accuracy, and the like. The chart on the right then shows how the response heats and cools. The rate of heating/cooling and size of increase are characteristic of, for example, the thermal diffusion of the fluid sample.

The above described FIGS. 14 to 18 are unfiltered output results, however the results may be filtered before display or use in further assessment of the fluid medium sample using the results of the micro-cantilever(s) responses. For example, the results may be band pass or bypass filtered. FIGS. 14 to 17 in particular show how the micro-cantilevers may be adjusted to be thermally dominant, or mechanically dominant—which may be seen from how the oscillations may be dominant (i.e. the whole signal oscillates—FIG. 15), or merely a "wobble" on the dominant thermal peak height response (FIG. 16).

Put another way, use of very short pulses (0.5 ms or shorter) result in predominantly having mechanical response. As the pulses become longer (say 1 order of magnitude) the thermal response is more present and the balance of the mechanical and thermal components will heavily depend on the fluid medium sample's viscosity and thermal properties, and thereby help characterise/measure them. Finally, with 2 orders of magnitude longer pulses (i.e., for example, 50 ms vs 0.5 ms) the response is almost entirely composed of the thermal component although in AC, a small initial contribution of the mechanical component is detectable. Thus, moving between the different mode types (i.e. mechanical or thermal dominant sensing modes) can provide very accurate characterisation of a particular fluid medium sample under test, especially when the micro-cantilever is suitably pre-calibrated.

Where the term 'mixer' is used above, this may be interchanged with the term 'agitator'. This is because the significant cantilever movement/deflection (e.g. >50 microns tip deflection for a cantilever of 100-800 microns length, preferably 200-800 microns, and width of 80 to 300 microns) in fluids, of the one or more micro-cantilevers used in embodiments may not actually mix, but rather simply agitate the fluid sample mixture. This is particularly the case where the fluid medium sample includes significant particulates (e.g. as formed when the fluid medium sample reacts with one or more reagents—see FIG. 6 for action in a particulate containing fluid). Equally, 'mixing effect' may be referred to as 'agitation'.

The disclosed method and device also has low power requirements compared to singular operation of standard known fluid medium sample thermal testing methods, such as the 'hot wire' test.

The excitation and measurement device may form part of a dynamic micro test/diagnostic system that is sensitive to the measurement of multiple fluid medium properties The design and fabrication of the hybrid micro-actuator of the micro test/diagnostic system may be such that it is tuned to be more/less responsive to thermal characteristics and/or mechanical characteristics in a hybrid sensor that may perform either or both mechanical and thermal measurements (e.g. choice of sensor material gauge factor and temperature coefficient of resistance, and choice of cantilever materials and thickness are adjustable to intrinsic physical behaviour or neutral axis of the probe).

Thus, it is possible to provide a simultaneous thermo-mechanical probing of a fluid medium sample using a multi-parameter probe (comprises one or more micro-cantilevers). Embodiments also provide the ability to scale thermal vs mechanical probing using a single probe and/or even a single pulse (or plurality of probes and/or plurality of pulses) as described above. This scaling anility may be thought of as the ability to slide the operation between fully thermal probing at one end, through to fully mechanical at the other, with varying degrees of thermo-mechanical sensing/probing in between.

This ability stems from the mixed thermal and mechanical characteristics of the micro-cantilever equipped with sensitive thermal and mechanical sensory portions. Moreover, the micro-cantilevers according to embodiments of the invention have the ability to be (relatively) thin, yet have a large surface vs small volume, which are elastic, and able to sweep >50 um in fluids/liquids, with or without particulates therein. The choice of thermo-mechanical mode of operation (i.e. whether the probing sensor(s) are tuned to be more thermally sensitive or more mechanically sensitive) will greatly depend on the nature of the reaction/sample at hand (i.e. to be tested) and/or the rheological changes that it will or likely undergo (e.g., but not limited to: aggregation, agglutination, segregation, separation, sedimentation, size of particles in the suspension, etc), as well as whether the changes are on the surface of the cantilever or affecting a larger volume of the fluid medium sample.

Embodiments of the invention provide a dynamic micro-actuator (i.e. in that it can have large sweeping deflection in fluids >50 microns) with integrated sensor for simultaneous detection of multiple properties of a fluid medium sample, including specific antigen antibody interactions. Preferably, the micro-actuator is a micro-cantilever based sensor.

The micro-cantilever based actuator used in embodiments may sense fluid/coagulate properties using thermal and/or movement based physical property measurements of the fluid medium. For example, the AC coupled electrical response for short pulses (i.e. <2 ms pulse width and peak power >100 mW) in a fluid has dominant mechanical characteristics (e.g. viscosity, density), the DC coupled electrical response for short pulses (i.e. <5 ms pulse width and peak power >100 mW) in a fluid has mechanical and thermal (e.g. thermal conductivity, temperature) characteristics, and the DC or AC coupled electrical response for long pulses (i.e. >50 ms pulse width with average power <15 mW) has a transient profile and absolute change in signal having dominant thermal characteristics only. This scaling of the mechanical and thermal dominance of the signal can be exploited to provide simultaneous measurements of both physical characteristics wherein the proportion can be tuned to the reaction to be measured (e.g. in the fluid volume, or in proximity to the probe, or on the surface of the probe, all achievable because the micro-cantilevers are fully movable between physical extremes of movement that can encompass a large proportion of the fluid medium sample). Put another way, the micro-cantilevers as arranged according to embodiments described herein are so moveable, they can sense the fluid medium sample in many more ways that prior art methods would allow—i.e. the micro-cantilever sensors are fully movable in the volume of the fluid medium sample.

The above-described suitable calibration tests may comprise using the micro-cantilever probe in Glycerol/water mixtures which may be used to provide calibrated micro-cantilever response characteristics. These may then be used in conjunction with pre-fluid characterisation tests (i.e. in air) to standardise the micro-cantilever operation before fluid medium sample testing.

FIG. 10 above shows the DC coupled electrical response in a Wheatstone quarter-bridge of a single exemplary micro-cantilever device in 0 to 99 percentage weight glycerol with respect to water solutions (as described in more detail in Table 1), and particularly shows the ability of the micro-cantilever sensor arranged according to embodiments of the invention to provide both rheological and thermal properties of the medium under a suitable calibration using a single actuation pulse. The single electrical signal could also be coupled into electrical AC components that have a dominance of mechanical signal. This is to say, the DC response may come from the steady state form of activation, with a single relatively long and low power pulse, and the AC components may come from the relatively short pulse(s) that are detecting mechanical properties.

The micro-cantilever sensor may be arranged to provide for simultaneous multi-parameter sensing (thermal and mechanical) that has unique attributes e.g. enhanced agitation (through increased or specific forms of sweep motion). For example, the DC coupled electrical response for short pulses (i.e. <5 ms pulse width and peak power >100 mW) in a fluid has both mechanical and thermal (e.g. thermal conductivity, temperature) characteristics.

When designing a multi-parameter fluid medium sample probe, it is possible to combine a simultaneous thermal measurement with a mechanical (viscosity) micro-cantilever fluid probe. Such a system may be arranged so that in a single low energy pulse (e.g. <5 ms pulse width having <1 mJ of dissipated energy), it is possible to be able to extract measurements for multiple characteristics of a fluid medium, including but not limited to: viscosity, thermal conductivity, heat capacity, density, and temperature. This may be optimised by selecting a piezo-resistor material that is approximately equal in sensitivity to both mechanical bending and temperature for the current fluid probe operation, e.g. NiChrome (NiCr) would be suitable choice. The design and operation of the micro-cantilever may also be arranged such that the dominance of signal due to thermal compared to mechanical properties of the medium is tuned for the desired application (e.g. For a reaction in the fluid volume, the thermal response characteristics of temperature and thermal conductivity allow probing in this space while the mechanical signal could provide information on the flow and movement of the fluid, whereas for a reaction on the surface of the micro-cantilever the mechanical damping of the signal indicates the reaction while the thermal signal could be used as a secondary confirmation).

For a multi-parameter sensing probe, for example for use in combined thermal and mechanical sensing, a typical pulse width would be 1-5 ms, with peak or average energy of 0.1-2.5 mJ, as detailed below:

| Type of Measurement | Typical Pulse Width | Typical Peak Power | Typical Average Power | Typical Pulse Energy |
|---|---|---|---|---|
| Combined Thermal and Mechanical | 1-5 ms | 100-500 mW | 10-50 mW | 0.1-2.5 mJ |

Where use alternative long and short pulse use is described, these may take the form of, e.g., 1-5 ms (for short) and then up to 50 ms (for long) pulse widths, respectively, thereby providing both the dominant mechanical (in the case of the short pulse) and then dominant thermal (in the case of the longer pulse) sensing portions. The thermal and mechanical properties of interest may then be extracted from the observed responses, by using the calibrated micro-cantilever response characteristics from previous initial tests in known fluid medium samples, such as air, varying glycerol mixtures, or the like. The above described "quantitative" measurements may also be derived from the calibrated micro-cantilever response characteristics from initial tests.

In the above description, "low" may include "near zero", CuNi is also known as Constantan, and the piezo-resistor may be formed of NiChrome (NiCr). Where testing of a fluid medium sample is mentioned, it includes any reaction with the fluid medium sample or therein. In the above descriptions of the mechanical or thermal sensing modes are described, these discussion equally apply to situations where the respective sensing mode is dominant, rather than only/sole mode in use.

In any of the above described embodiments, the coating(s) of the micro-cantilever may be omitted, i.e. the described apparatuses may be used with or without coatings.

A 'multi-parameter one pulse design' may also be realised, in which a single low energy pulse (or sufficiently spaced apart multiple pulses) may be used to activate/actuate the one or more micro-cantilevers. This is a form of sensor which can measure several of the above-described properties (e.g. thermal conductivity, diffusivity, viscosity, density, etc) of the fluid medium sample, either at a single point in time when the low energy pulse is applied (e.g. after a reaction has occurred, for example, to characterise the result of the reaction), or over a predetermined period/length of time by pulsing regularly, but sufficiently far apart in time for each individual pulses to dissipate before the next pulse is applied (e.g. to detect changes to the fluid medium sample due to/whilst the reaction in the fluid medium sample occurs). The exact level of "low energy" is dependent on a number of physical factors of the micro-cantilevers(s) being used, such as materials used, dimensions of cantilever or its component parts, and the like, and potentially the fluid medium sample being put under test.

Where sufficiently spaced apart multiple pulses are used instead of a single pulse, these may be achieved, for example, by using a repeating pulse generator with a pulse width modulation applied such that the "on" period is relatively small compared to the "off" period—i.e. a variable duty cycle.

A functional definition of low energy pulse' may be a pulse with low enough energy to not cause any direct heating of the sample by the heater arrangement within the micro-cantilever, through the two layers of material having different coefficients of thermal expansion (e.g. polyimide layers), yet sufficient energy to move/deflect the micro-cantilever to a deflected position that allows the micro-cantilever to properly sweep through the fluid medium sample. However, suitable selection of the micro-cantilevers' materials, particularly the two materials having different thermal coefficients of expansion used in the bi-morph portion may be used to contain the heat sufficiently within the cantilever to avoid excessive heat leakage into the fluid medium sample. Use of polyimide layers having different thermal coefficients of expansion is particularly useful in this respect, compared to using, for example, silicon or a metal, due to this material's comparatively low thermal conductivity and diffusivity (see table 2 above).

The form of low energy pulse used may be any suitable input signal shape, such as square, sinusoid, triangular, sawtooth or the like. The input signal shape may also be any arbitrary digitally produce signal, depending on the needs of a particular test. The different shapes would provide, in effect, different ramp heating and therefore different mechanical response (shear) and thermal response over the signal pulse period. Digitally formed pulses may provide complete control over the instantaneous heating profile being applied to the at least one micro-cantilevers. However, a currently preferred pulsing technique is to use a square wave formation. In this case, the energy level is a function of the length of the duty cycle, and the peak output level—and thus the energy level is adjustable by changing either or both of these values.

The above described embodiments of the present invention may provide a parallel function of a mixer (of the fluid medium sample under test), because it is capable of (relatively) large sweeps (i.e. movement of the free end of the micro-cantilever), compared to its length. This means the sweep may be truly out of plane (relative to the plane of the micro-cantilever main bar). For example, embodiments of the present invention may exhibit sweeps where L/R is 0.15, where R is radius of curvature of the main bar/beam of the micro-cantilever, and L is the length of the micro-cantilever (and noting that a half circle would be L/R=Pi=3.14). For example, with a beam length of 600-800 μm, it is possible to achieve a (very) curled state of between 200-400 microns deflection. Embodiments of the micro-cantilever(s) used are capable of going from very curled down to very flat (e.g., about 55 microns deflection for a 750 micron beam). In some embodiments, the micro-cantilever may be held completely flat.

Properties that may be measured include but are not limited to thermal conductivity, heat capacity, density, volumetric heat capacity, heat convection coefficient, and thermal diffusivity, which are all particularly measurable using embodiments of the present invention which use polyimide as the basis for the bi-morph layers of the micro-cantilever. This is, at least partly, due to the significant differences between the thermal characteristics of silicon or a metal such as aluminium used (as one or both of the bi-morph layers) in prior cantilevers, compared to polyimide.

| Substance | Thermal Capacity | Thermal Conductivity | Thermal Diffusivity |
|---|---|---|---|
| Water at 20° C. | 1 [Cal/cm$^3 \cdot$ ° C.] | 0.0014 [Cal/s $\cdot$ cm $\cdot$ ° C.] | 0.0014 [cm$^2$/s] |
| Alcohol, ethyl | 0.000319 [Cal/cm$^3 \cdot$ ° C.] | 0.0004063 [Cal/s $\cdot$ cm $\cdot$ ° C.] | 1.2737 [cm$^2$/s] |
| Air at 20° C. | 0.000289 [Cal/cm$^3 \cdot$ ° C.] | 0.000057 [Cal/s $\cdot$ cm $\cdot$ ° C.] | 0.19706 [cm$^2$/s] |

The table above lists some of the most important parameters in the dynamic thermal model, where:

Thermal Conductivity=the rate at which heat is transferred by conduction through a unit cross-sectional area of material when a temperature gradient exists perpendicular to the area. The coefficient of thermal conductivity is expressed as the quantity of heat that passes through a unit cube of the substance in a given unit of time when the difference in temperature of the two faces is 1 degrees Celsius.

Thermal Capacity, is linked to the specific heat of materials (specific heat density), and it is the quantity of heat necessary to produce a unit change of temperature in a unit mass of a substance, or in other words, the ability of a material to store heat.

Thermal Diffusivity describes the rate at which heat is conducted through a medium. It is related to thermal conductivity and thermal capacity (ratio), where a high thermal diffusivity inhibits convection.

Finally, increasing the length, thickness and width of the cantilevers increases the overall surface and thus the heat losses by convection and conduction mechanisms. For comparison, a 10-fold increase of all dimensions would result in 100-fold greater cantilever surface.

The micro-cantilever(s) may be energised into a steady state with an extended length pulse, where an "extended length pulse" or "energised into steady state" may for example be the application of an actuating signal for between 5 and 200 ms. Alternatively, the micro-cantilevers may operate as a combined mechanical and thermal property sensing sensor, which allows different mechanical and thermal properties to be measured in a single pulse (of, for example, between 1 and 5 ms).

Directionality of bending/curling—the micro-cantilevers may be formed to bending in either direction when the actuating heat is applied—in the forgoing example embodiments, the micro-cantilever(s) are formed such that they bend up, out of plane, when a single is applied, and drop back into plane as the actuating signal is removed, and the heart generated dissipated away.

Embodiments described above include a method and apparatus for active differential sensing of reactions in a fluid medium sample under test using two or more micro-cantilevers, i.e. one that actuates both first and second micro-cantilevers simultaneously. When activating in this way both responses (i.e. the output signal) of the respective micro-cantilevers have a signal and background noise, and the described differential method is then "a measure of the difference between two active signals". This is in contrast to previous differential methods that do not activate one of the micro-cantilever sensors in a differential test, i.e. what we may call passive differential test, or "a measure of the difference between one active signal and background noise". This difference between the active differential sensing described above, and the known passive differential sensing may be best illustrated mathematically (for the case of two micro-sensors, but can be extrapolated up to any number of micro-cantilevers, accordingly) as:

Passive differential sensing=(SIG $A$+DRIFT)$_{cantilever1}$−(DRIFT)$_{cantilever2}$=(SIG $A$)

Whereas the above described active differential embodiments of the present invention=(SIG A+DRIFT)$_{cantilever1}$−(SIG B+DRIFT)$_{cantilever2}$=(SIG A−SIG B), Where DRIFT is the background noise induced drift in responses between the two identical (other than, for example, coating) micro-cantilevers. Thus, the above described active differential method may be a true differential measure of the different sensor outputs. In such a way, the active differential sensing method may be used, for example, to allow the tracking of the progress of a reaction or similar. This may be done in particular where the micro-cantilevers according to embodiments of the present invention are located within, or on a surface of, a greater (i.e. larger) sized vessel, e.g. a production vat or vessel, containing (a macro-sample) of the one or more fluids under test (including reagent, where applicable), and those micro-cantilevers are formed in an array or physical selection of locations around or within the vessel, so that the outputs of each sensor can be compared directly, without drift, and therefore are able to track the "wave front" of a moving reaction. Alternatively, these arrays can simply detect where final fully mixed/fully reacted portions of the fluid medium sample are located, relative to portions where the reaction is still yet to occur, or complete. This is because each micro-cantilever is substantially identical (through identical mass production on the same wafer), and by using the active differential comparison method described above, it allows, for example, comparing the output of a cantilever at the very bottom of a production vat of some mixture (including multiple base fluids and reagents, as appropriate for the respective production) with the very top where the (latest) substance was added—e.g. in the production of mayonnaise, the addition of oil to egg yolks. Here a suitably formed and positioned array (of any suitable number) of micro-cantilevers arranged to carry out the differential sensing method would allow the progress of the emulsification of the oil with/by/into the egg yolk to be tracked. This clearly may be applied to any process in which a change in physical properties of a medium can be useful in knowing when the process is complete, not over worked, etc—especially industrial processes that are otherwise more difficult to assess in real-time).

The shape of the array of micro-cantilevers may also help for a particular use case—for example, where the spread of a reaction is needed to be tracked across an area, the array may be formed such that it is in the general form of a set of points in, for example, concentric rings around the reagent entry point.

Put another way, the active differential sensing method and apparatus embodiments of the present invention may measure the (changing) properties of the fluid under test, rather than properties of the micro cantilever(s) itself. This may be particularly important where the reaction to be measured is all within the fluid under test itself, and not in any way started or accelerated by the micro-cantilevers themselves, which may otherwise occur when the cantilevers have reagent on them, and/or apply other sensing techniques, such as using "added mass" on the cantilever (usually detected by detecting a change a resonant frequency, or the like), "binding" on the cantilever type sensing (similarly detecting a change in resonant frequency, or the like), or "exothermic temperature".

The output signal(s) of the at least one micro-cantilever(s) may be sampled at any point after the electrical pulse (to heat the integrated heater of the micro-cantilever) has been applied, dependent on requirements of the test. A suitable useful range may be 1 ms to 1 second, more preferably between 1 ms and 200 ms, or even 50 to 100 ms.

Note the different micro-cantilevers described in any embodiment above, especially the differential sensing embodiments, may have any of: different coatings applied to each micro-cantilever, the same coating applied to both/all micro-cantilevers, or no coatings applied to either/all micro-cantilevers. The different coating regimes may occur, for example, because:

For use cases where no coatings are applied, this means only the fluid (mixture) under test itself is being analysed, and not any form of reaction based upon the coating(s)—this is particularly useful where the fluid under test can be/needs to be spiked with a reagent at a certain point in time, and the whole of the test results, from before spiking, through spiking itself, to 'end steady state' (where applicable) after spiking can be detected, analysed and the results monitored.

For use cases where different coatings may be applied, for example different reactionary tests can be carried out in the same bulk fluid (e.g. to provide different reagent based reaction comparative testing). For example, a first cantilever may be coated with a first reagent in order to apply a first reagent based test, to determine a first parameter about the bulk fluid under test, then a second cantilever may be coated with a second reagent in order to apply a second reagent based test, to determine a second parameter about the bulk fluid under test. This may be extrapolated up to any suitable number of individual tests involving different coatings of different cantilevers.

Nothing in this description is to be taken as limiting the embodiments or claims to only the described selection of features as currently claimed and other selections of features are also contemplated, but not listed out in full, in order to not obscure the description of the invention. Thus, the order and claim numbering is not to be construed as a limitation as to the feature selection and combination, unless said feature combination is a physical impossibility. As may be appreciated, different feature selections may have different synergistic effects that lead to useful and important diagnostic or monitoring abilities, and those combinations have also been contemplated, but not listed out in full to avoid confusion.

The invention claimed is:

1. A method of monitoring one or more specified reactions in a fluid medium sample using a thermal and/or mechanical signature, said method comprising:
providing at least one micro-cantilever sensor, said micro-cantilever sensor comprising at least two materials having different coefficients of thermal expansion, and having a heater and piezo-resistive sensor integrated therein;
calibrating the at least one micro-cantilever response to thermal changes to form a calibrated micro-cantilever response characteristic;
starting a specified reaction in the fluid medium sample;
pulsing the heater with one or more electrical pulses to induce heat generation in the micro-cantilever sensor;
biasing a controlled environment surrounding the at least one micro-cantilever sensor by heating the fluid medium sample to a predetermined temperature, by providing a constant Direct Current (DC) offset to the one or more electrical pukes supplied to the heater;
sampling an output of the integrated piezo-resistive sensor to characterise a response of the micro-cantilever during the specified reaction in the fluid medium sample; and
subtracting the calibrated micro-cantilever response characteristic from the sampled output to determine a characteristic of the one or more specified reactions in the fluid medium sample.

2. The method of claim 1, further comprising tuning the at least one micro-cantilever sensor to be more thermally sensitive, or more mechanically sensitive, on a sliding scale between the two, dependent on a test to be carried out on the fluid medium sample.

3. The method of claim 1, wherein using a thermal signature comprises using a thermal and mechanical signature, and wherein calibrating the at least one micro-cantilever response further comprises calibrating to thermal and mechanical changes.

4. The method of claim 1, wherein the one or more specified reactions include one or more reactions selected from a group consisting of: a covalent reaction; a non-covalent reaction; a binding reaction; a non-binding reaction; an antibody-antigen reaction; an agglutination reaction; and a blood typing reaction.

5. The method of claim 1, wherein the characteristic of the one or more specified reactions in the fluid medium sample is the presence or not, or extent, of the one or more specified reactions.

6. The method of claim 1, further comprising coating the at least one micro-cantilever sensor with a reagent for at least one of the one or more specified reactions.

7. The method of claim 1 comprising providing at least two substantially similar micro-cantilevers, wherein one is coated with a reagent, and one is uncoated, wherein the method further comprises comparing an output of a piezo-resistive sensor integrated into the coated micro-cantilever with an output of a piezo-resistive sensor integrated into the uncoated micro-cantilever when both are immersed in the fluid medium sample.

8. The method of claim 1, wherein calibrating the at least one micro-cantilever response further comprises calibrating to thermal and mechanical changes of a known fluid.

9. The method of claim 1 comprising determining at least one thermal property of the fluid medium sample selected from a group consisting of: thermal conductivity; heat capacity; temperature; volumetric heat capacity; and thermal diffusivity.

10. The method of claim 1, wherein operation of the at least one micro-cantilevers sensor during testing is operable to accelerate a reaction occurring within the fluid medium sample under test.

11. The method of claim 1, wherein the biasing is beneficial for a specific antigen-antibody interaction being sought or tested.

* * * * *